United States Patent
Rigo et al.

(10) Patent No.: US 10,851,371 B2
(45) Date of Patent: Dec. 1, 2020

(54) MODULATION OF SMN EXPRESSION

(71) Applicants: Ionis Pharmaceuticals, Inc., Carlsbad, CA (US); The Johns Hopkins University, Baltimore, MD (US)

(72) Inventors: Frank Rigo, Carlsbad, CA (US); C. Frank Bennett, Carlsbad, CA (US); Constantin Van Outryve D'Ydewalle, Baltimore, MD (US); Charlotte J. Sumner, Baltimore, MD (US)

(73) Assignees: Ionis Pharmaceuticals, Inc., Carlsbad, CA (US); The Johns Hopkins University, Baltimore, MD (US)

( * ) Notice: Subject to any disclaimer, the term of this patent is extended or adjusted under 35 U.S.C. 154(b) by 177 days.

(21) Appl. No.: 15/565,488

(22) PCT Filed: Apr. 11, 2016

(86) PCT No.: PCT/US2016/026928
§ 371 (c)(1),
(2) Date: Sep. 20, 2018

(87) PCT Pub. No.: WO2016/164896
PCT Pub. Date: Oct. 13, 2016

(65) Prior Publication Data
US 2018/0273943 A1    Sep. 27, 2018

Related U.S. Application Data

(60) Provisional application No. 62/146,052, filed on Apr. 10, 2015.

(51) Int. Cl.
*C12N 15/113* (2010.01)
*C07H 21/02* (2006.01)
*C12Q 1/68* (2018.01)

(52) U.S. Cl.
CPC .......... *C12N 15/113* (2013.01); *C07H 21/02* (2013.01); *C12N 2310/11* (2013.01); *C12N 2310/113* (2013.01); *C12N 2310/315* (2013.01); *C12N 2310/321* (2013.01); *C12N 2310/3231* (2013.01); *C12N 2310/3341* (2013.01); *C12N 2310/341* (2013.01); *C12N 2310/345* (2013.01); *C12N 2310/346* (2013.01)

(58) Field of Classification Search
None
See application file for complete search history.

(56) References Cited

U.S. PATENT DOCUMENTS

| | | | |
|---|---|---|---|
| 6,210,892 | B1 | 4/2001 | Bennett et al. |
| 6,998,259 | B1 | 2/2006 | Davis et al. |
| 9,717,750 | B2 | 8/2017 | Bennett et al. |
| 10,436,802 | B2 | 10/2019 | Rigo et al. |
| 2008/0064084 | A1 | 3/2008 | Muller et al. |
| 2011/0294868 | A1 | 12/2011 | Monia et al. |
| 2017/0363643 | A1 | 12/2017 | Rigo et al. |
| 2018/0291376 | A1 | 10/2018 | Baker et al. |
| 2019/0030058 | A1 | 1/2019 | Bennett et al. |

FOREIGN PATENT DOCUMENTS

| | | |
|---|---|---|
| WO | WO 2016/164896 | 10/1916 |
| WO | WO 2003/037909 | 5/2003 |
| WO | WO 2010/148249 | 12/2010 |
| WO | WO 2012/178146 | 12/2012 |
| WO | WO 2013/173638 | 11/2013 |
| WO | WO 2014/110291 | 7/2014 |
| WO | WO 2015/023941 | 2/2015 |
| WO | WO 2015/051283 | 4/2015 |
| WO | WO 2015/161170 | 10/2015 |

OTHER PUBLICATIONS

Bennett et al. Biochimica et Biophyica Acta vol. 1489:19-30, 1999.*
Zhang et al., "An in vivo reporter system for measuring increased inclusion of exon 7 in SMN2 mRNA: potential therapy of SMA" Gene Ther (2001) 8(20): 1532-1538.
Cartegni et al., "Disruption of an SF2/ASF-dependent exonic splicing enhancer in SMN2 causes spinal muscular atrophy in the absence of SMN1", Nat. Genet., (2002) 30:377-384.
D'Ydewalle. LncRNA as therapeutic target for SMA [online] Jan. 30, 2015 [retrieved Aug. 11, 2015 by ISA/US].
D'Ydewalle "Possible functions of SMN-associated long non-coding RNAs" Johns Hopkins Medicine Apr. 10, 2014.
D'Ydewalle "The long non-coding RNA SMN-AS1 as therapeutic target for SMA" 2016 FightSMA 25th Anniversary Conference Presentation.
Genbank Accession No. BC045789.1.
Lefebvre et al., "The Role of the SMN Gene in Proximal Spinal Muscular Atrophy" Hum. Mol. Genet. (1998) 7(10):1531-1536.
International Search Report for application PCT/US2016/026928 dated Sep. 27, 2016.
Davis et al., "Potent inhibition of microRNA in vivo without degradation," Nucleic Acids Res, 2009, 37:70-77.
Khoo et al., "Splicing therapeutics in SMN2 and APOB," Curr Opin Mol Ther, 2009, 11:108-115.
Kiraly et al., "Expression of human cationic trypsinogen with an authentic N terminus using intein-mediated splicing in aminopeptidase P (pepP) deficient *Escherichia coli*," Protein Exp Purif, 2006, 48:104-111.
Koller et al., "Use of a Chemically Modified Antisense Oligonucleotide Library to Identify and Validate Eg5 (Kinesin-Like 1) as a Target for Antineoplastic Drug Development," Cancer Res, 2006, 66:2059-2066.
Miller et al., "Gene-Target Therapies for the Central Nervous System," Arch Neurol, 2008, 65:447-451.
Sloop et al., "Hepatic and glucagon-like peptide-1-mediated reversal of diabetes by glucagon receptor antisense oligonucleotide inhibitors," J Clinical Invest, 2004, 113:1571-1581.

(Continued)

*Primary Examiner* — Sean McGarry
(74) *Attorney, Agent, or Firm* — McNeill Baur PLLC

(57) ABSTRACT

Certain embodiments are directed to methods and compounds for inhibiting SMN-NAT, the natural antisense transcript of SMN. Such methods and compounds are useful for increasing expression of SMN in cells and animals.

21 Claims, No Drawings
Specification includes a Sequence Listing.

(56) References Cited

OTHER PUBLICATIONS

Wilcox et al., "Immobilization and Utilization of the Recombinant Fusion Proteins Trypsin-Streptavidin and Streptavidin-Transglutaminase for Modification of Whey Protein Isolate Functionality," J Agricult Food Chem, 2002, 50:3723-3730.
Kobayashi et al., "Evaluation of peripheral blood mononuclear cell processing and analysis for Survival Motor Neuron protein" PLoS One (2012) 7(11): e50763.
Nguyen et al., "A two-site ELISA can quantify upregulation of SMN protein by drugs for spinal muscular atrophy" Neurology (2008) 71(22): 1757-1763.
Piepers et al., "Quantification of SMN protein in leucocytes from spinal muscular atrophy patients: effects of treatment with valproic acid" J Neurol Neurosurg Psychiatry (2011) 82(8): 850-852.
Rigo et al., "Pharmacology of a central nervous system delivered 2'-O-methoxyethyl-modified survival of motor neuron splicing oligonucleotide in mice and nonhuman primates" J Pharmacol Exp Ther (2014) 350(1): 46-55.
Shukla et al., "Quantitative determination of human interleukin 22 (IL-22) in serum using Singulex-Erenna® technology" J Immunol Methods (2013) 390: 30-34.
Todd et al., "Ultrasensitive flow-based immunoassays using single-molecule counting" Clin Chem (2007) 53(11):1990-1995.
D'Ydewalle et al., "The Antisense Transcript SMN-AS1 Regulates SMN Expression and Is a Novel Therapeutic Target for Spinal Muscular Atrophy" Neuron (2017) 93: 66-79.
Kramer et al., "Raise the Roof: Boosting the Efficacy of a Spinal Muscular Atrophy Therapy" Neuron (2017) 93: 3-5.
Woo et al., "Gene activation of SMN by selective disruption of lncRNA-mediated recruitment of PRC2 for the treatment of spinal muscular atrophy" Proc Natl Acad Sci USA (2017) 114: E1509-E1518.
Zhou et al., "Targeting RNA-splicing for SMA Treatment" Molecules and Cells (2012) 33: 223-228.
Partial Search Report for EP 17814164.4 dated Jan. 23, 2020.
Extended Search Report for EP 17814164.4 dated Jun. 5, 2020.

\* cited by examiner

SEQUENCE LISTING

<160> NUMBER OF SEQ ID NOS: 79

<210> SEQ ID NO 1
<211> LENGTH: 1613
<212> TYPE: DNA
<213> ORGANISM: Homo sapiens

<400> SEQUENCE: 1

```
agtaattaaa agtgtagtac tgacatcaat atacactaat agacaatgta acagaattga      60
gagtcagaaa tagccctgtg atatatgtga ctgattttaa ctaaagttac aaatgtggtt     120
taatagagaa agcatagtag tttcaagaaa tggtggtaaa actattggaa atccttatgc     180
aaaaacaaac caaatttcca cctacactga gccacatata agaattaata caaaatggat     240
tacagaccta agtgtaaaac taaaactcta aactgtgtaa aaaaaaaaaa gagagaaaaa     300
tctgtgatca tggattgcct ataacaaaag aacaaactga aatggccttg ttgcctgggg     360
tggcacccga ggttcttggt ctcacgctga ggaaatcaag gacgctgaca caccaagggt     420
gtgaggctag agcagaagtt taataggcaa aagaaagaga ctagctctct cctgcagaga     480
gaggtcctga aaagagttcc cattccacag tgaaatgcaa gcatttttat aaatgagcta     540
atgggaaggg ggtagcttat ctacacatag ggagcaaaaa accagttagg accaggtgtt     600
gccatctgca cagagcgtga atctctggca tcccccaccc caacctttta ttatgcaggc     660
aggtccttgg cctgagctac tccacattgc ttatctcttt cctattgtgc atgtgctaaa     720
taagggagg tggagccacc atggtggaca tgcctggccc caggtacccc tttctctccg     780
tgcagctgca ggcaacccca acaactcaca acatgcaagc ttccagcttc cttatctgag     840
tatgtactaa ggtccactgt gtttacttca catactgtgt ttacttcaca tacccacctt     900
acgtatgtga agcttgctga ttacccagga agctcccct ctgtgccaga gctgcttcct     960
tatacatgtt tacagcccga tcttccaggc tgctccttgt tagaagagaa gtgatttctt    1020
gggctgcttt ttgttagaag ggaagttcta ccgaggactc tgtctaacta tcggcttacc    1080
tagtcttttt ttacctcctc tctcaaaacc atcaaagaaa aaactgaaaa attagatttc    1140
agcaaaatta agattttctg ttcttaaaaa gacgttgtta acaaaatgaa aaaccaaagt    1200
gtaaaccggg agaaaataca tgcaagttac ctatctgata aagatattgt acccagcaaa    1260
catgaagaac tctcaaacct caacaacaaa aaaattcaat taaagatgg gtaagttggc    1320
cgggtgcagt ggctcatact tgcaatccca atctttggga ggctgaggca ggaagattgc    1380
ttgagcccag gagttcacga caagcccagg caacataatg agaccttgtt tctacaaaat    1440
tttaaaaaat tagccaggca ttgtggcgtg tgctcgtaat ttcagctact cagaaggctg    1500
```
agacaagaag actgagcgca ggaggtggag gctgcagtag gctgtgtgat tgcaccactg    1560
cacaacagcc tgggtgacag agtgagacac tgtctccaaa aaaaaaaaaa aaa           1613

<210> SEQ ID NO 2
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2
gtactacact tttaattact                                                 20

<210> SEQ ID NO 3
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 3
tgtatattga tgtcagtact                                                 20

<210> SEQ ID NO 4
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 4
tacattgtct attagtgtat                                                 20

<210> SEQ ID NO 5
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 5
tgactctcaa ttctgttaca                                                 20

<210> SEQ ID NO 6
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 6
tcacagggct atttctgact                                                 20

<210> SEQ ID NO 7
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 7
aatcagtcac atatatcaca                                                 20

<210> SEQ ID NO 8
<211> LENGTH: 20

```
<212> TYPE: DNA
<213> ORGANISM: Artificial sequence
<220> FEATURE:
<223> OTHER INFORMATION: Synthetic oligonucleotide

<400> SEQUENCE: 8 tgtaaccttta gttaaaatca                                              20

<210> SEQ ID NO 9
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 9
ctattaaacc acatttgtaa                                               20

<210> SEQ ID NO 10
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 10
actactatgc tttctctatt                                               20

<210> SEQ ID NO 11
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 11
ccaccatttc ttgaaactac                                               20

<210> SEQ ID NO 12
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 12
tttccaatag ttttaccacc                                               20

<210> SEQ ID NO 13
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 13
gtttttgcat aaggatttcc                                               20

<210> SEQ ID NO 14
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 14
```

```
gtggaaattt ggtttgtttt                                              20

<210> SEQ ID NO 15
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 15
tgtggctcag tgtaggtgga                                              20

<210> SEQ ID NO 16
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 16
gtattaattc ttatatgtgg                                              20

<210> SEQ ID NO 17
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 17
ttagttttac acttaggtct                                              20

<210> SEQ ID NO 18
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 18
acacagttta gagttttagt                                              20

<210> SEQ ID NO 19
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 19
gatcacagat ttttctctct                                              20

<210> SEQ ID NO 20
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 20
ttataggcaa tccatgatca                                              20

<210> SEQ ID NO 21
<211> LENGTH: 20
<212> TYPE: DNA
<213> ORGANISM: Artificial sequence
```

<220> FEATURE:
<223> OTHER INFORMATION: Synthetic oligonucleotide

<400> SEQUENCE: 21
catttcagtt tgttcttttg                                               20

<210> SEQ ID NO 22
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 22
cccaggcaac aaggccattt                                               20

<210> SEQ ID NO 23
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 23
gaacctcggg tgccacccca                                               20

<210> SEQ ID NO 24
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 24
cgtccttgat ttcctcagcg                                               20

<210> SEQ ID NO 25
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 25
acacccttgg tgtgtcagcg                                               20

<210> SEQ ID NO 26
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 26
ttctgctcta gcctcacacc                                               20

<210> SEQ ID NO 27
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 27
ggagagagct agtctctttc                                               20

<210> SEQ ID NO 28
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 28
aggacctctc tctgcaggag                                               20

<210> SEQ ID NO 29
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 29
atgggaactc ttttcaggac                                               20

<210> SEQ ID NO 30
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 30
gcatttcact gtggaatggg                                               20

<210> SEQ ID NO 31
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 31
tttataaaaa tgcttgcatt                                               20

<210> SEQ ID NO 32
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 32
cttcccatta gctcatttat                                               20

<210> SEQ ID NO 33
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 33
tagataagct accccttcc                                                20

<210> SEQ ID NO 34
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 34
tttgctccct atgtgtagat                                                    20

<210> SEQ ID NO 35
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 35
ggtcctaact ggtttttgc                                                     20

<210> SEQ ID NO 36
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 36
cagatggcaa cacctggtcc                                                    20

<210> SEQ ID NO 37
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 37
gattcacgct ctgtgcagat                                                    20

<210> SEQ ID NO 38
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 38
gcctgcataa taaaaggttg                                                    20

<210> SEQ ID NO 39
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 39
tcaggccaag gacctgcctg                                                    20

<210> SEQ ID NO 40
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 40
taagcaatgt ggagtagctc                                                    20

<210> SEQ ID NO 41

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 41
acaataggaa agagataagc                                              20

<210> SEQ ID NO 42
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 42
ttatttagca catgcacaat                                              20

<210> SEQ ID NO 43
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 43
tggctccacc tcccttatt                                               20

<210> SEQ ID NO 44
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 44
gcatgtccac catggtggct                                              20

<210> SEQ ID NO 45
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 45
agctgcacgg agagaaaggg                                              20

<210> SEQ ID NO 46
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 46
gcatgttgtg agttgttggg                                              20

<210> SEQ ID NO 47
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 47
```
tcagataagg aagctggaag         20

<210> SEQ ID NO 48
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 48
gaccttagta catactcaga         20

<210> SEQ ID NO 49
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 49
gaagtaaaca cagtggacct         20

<210> SEQ ID NO 50
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 50
gtatgtgaag taaacacagt         20

<210> SEQ ID NO 51
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 51
gtaaacacag tatgtgaagt         20

<210> SEQ ID NO 52
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 52
aggtgggtat gtgaagtaaa         20

<210> SEQ ID NO 53
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 53
atcagcaagc ttcacatacg         20

<210> SEQ ID NO 54
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 54
ggagcttcct gggtaatcag                                                20

<210> SEQ ID NO 55
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 55
agcagctctg gcacagaggg                                                20

<210> SEQ ID NO 56
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 56
aaacatgtat aaggaagcag                                                20

<210> SEQ ID NO 57
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 57
ggaagatcgg gctgtaaaca                                                20

<210> SEQ ID NO 58
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 58
acttctcttc taacaaggag                                                20

<210> SEQ ID NO 59
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 59
cagagtcctc ggtagaactt                                                20

<210> SEQ ID NO 60
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 60
aagccgatag ttagacagag                                                20
```

<210> SEQ ID NO 61
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 61
aaaaaaagac taggtaagcc                                          20

<210> SEQ ID NO 62
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 62
gttttgagag aggaggtaaa                                          20

<210> SEQ ID NO 63
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 63
gtttttcctt tgatggtttt                                          20

<210> SEQ ID NO 64
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 64
gaaatctaat ttttcagttt                                          20

<210> SEQ ID NO 65
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 65
aatcttaatt ttgctgaaat                                          20

<210> SEQ ID NO 66
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 66 ttttaagaa cagaaaatct                                           20

<210> SEQ ID NO 67
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 67
acactttggt ttttcatttt                                                20

<210> SEQ ID NO 68
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 68
attttctccc ggtttacact                                                20

<210> SEQ ID NO 69
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 69
aggtaacttg catgtatttt                                                20

<210> SEQ ID NO 70
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 70
aatatcttta tcagataggt                                                20

<210> SEQ ID NO 71
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 71
atgtttgctg ggtacaatat                                                20

<210> SEQ ID NO 72
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 72
gtttgagagt tcttcatgtt                                                20

<210> SEQ ID NO 73
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 73
catcttttaa ttgaattttt                                                20

```
<210> SEQ ID NO 74
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 74
cccggccaac ttacccatct                                              20

<210> SEQ ID NO 75
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 75
gattgggatt gcaagtatga                                              20

<210> SEQ ID NO 76
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 76
gagcacacgc cacaatgcct                                              20

<210> SEQ ID NO 77
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 77
agtcttcttg tctcagcctt                                              20

<210> SEQ ID NO 78
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 78
ccacctcctg cgctcagtct                                              20

<210> SEQ ID NO 79
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 79
tcacacagcc tactgcagcc                                              20
```

MODULATION OF SMN EXPRESSION

SEQUENCE LISTING

The present application is being filed along with a Sequence Listing in electronic format. The Sequence Listing is provided as a file entitled BIOL0274USASEQ_ST25.txt created Oct. 4, 2017 which is approximately 20 KB in size. The information in the electronic format of the sequence listing is incorporated herein by reference in its entirety.

FIELD

Certain embodiments are directed to methods and compounds for inhibiting SMN-NAT, the endogenous antisense transcript of Survival of Motor Neuron (SMN). Such methods and compounds are useful for inducing expression of SMN in cells and animals.

Background

Proximal spinal muscular atrophy (SMA) is a genetic, neurodegenerative disorder characterized by the loss of spinal motor neurons. SMA is an autosomal recessive disease of early onset and is currently the leading genetic cause of death among infants. The severity of SMA varies among patients and has thus been classified into three types. Type I SMA is the most severe form with onset at birth or within 6 months and typically results in death within 2 years. Children with type I SMA are unable to sit or walk. Type II SMA is the intermediate form and patients are able to sit, but cannot stand or walk. Patients with type III SMA, a chronic form of the disease, typically develop SMA after 18 months of age (Lefebvre et al., Hum. Mol. Genet., 1998, 7, 1531-1536).

The molecular basis of SMA is caused by the loss of both copies of survival motor neuron gene 1 (SMN1), which may also be known as SMN Telomeric, a protein that is part of a multi-protein complex thought to be involved in snRNP biogenesis and recycling. A nearly identical gene, SMN2, which may also be known as SMN Centromeric, exists in a duplicated region on chromosome 5q13 and modulates disease severity. Expression of the normal SMN1 gene results solely in expression of survival motor neuron (SMN) protein. Although SMN1 and SMN2 have the potential to code for the same protein, SMN2 contains a translationally silent mutation at position +6 of exon 7, which results in inefficient inclusion of exon 7 in SMN2 transcripts. Thus, the predominant form of SMN2 is a truncated version, lacking exon 7, which is unstable and inactive (Cartegni and Krainer, Nat. Genet., 2002, 30, 377-384). Expression of the SMN2 gene results in approximately 10-20% of the SMN protein and 80-90% of the unstable/non-functional SMN-delta7 protein. SMN protein plays a well-established role in assembly of the spliceosome and may also mediate mRNA trafficking in the axon and nerve terminus of neurons.

Antisense technology is an effective means for modulating the expression of one or more specific gene products, including alternative splice products, and is uniquely useful in a number of therapeutic, diagnostic, and research applications. The principle behind antisense technology is that an antisense compound, which hybridizes to a target nucleic acid, modulates gene expression activities such as transcription, splicing or translation through one of a number of antisense mechanisms. The sequence specificity of antisense compounds makes them extremely attractive as tools for target validation and gene functionalization, as well as therapeutics to selectively modulate the expression of genes involved in disease.

SUMMARY

Several embodiments provided herein relate to the discovery that antisense compounds targeting SMN-NAT increase expression of SMN. Several embodiments are drawn to methods and compounds for inducing expression of SMN using antisense compounds targeting SMN-NAT. Certain embodiments disclosed herein are drawn to a method of inducing expression of SMN in a cell comprising contacting the cell with an antisense compound targeted to SMN-NAT. In several aspects, SMN-NAT comprises a nucleic acid sequence at least 85% identical to SEQ ID NO:1.

The present disclosure provides the following non-limiting numbered embodiments:

EMBODIMENT 1

A method of reducing SMN-NAT in a cell, comprising contacting the cell with an antisense compound.

EMBODIMENT 2

A method of increasing expression of SMN in a cell, comprising contacting the cell with an antisense compound targeted to SMN-NAT.

EMBODIMENT 3

The method of embodiment 2, wherein the SMN is SMN2 mRNA.

EMBODIMENT 4

The method of embodiment 2, wherein the SMN is SMN2 pre-mRNA.

EMBODIMENT 5

The method of embodiment 2, wherein the SMN is SMN2 protein.

EMBODIMENT 6

The method of any of embodiments 1-5, wherein SMN-NAT comprises a nucleic acid sequence at least 85% identical to SEQ ID NO: 1.

EMBODIMENT 7

The method of any of embodiments 1-5, wherein SMN-NAT comprises a nucleic acid sequence at least 90% identical to SEQ ID NO: 1.

EMBODIMENT 8

The method of any of embodiments 1-5, wherein SMN-NAT comprises a nucleic acid sequence at least 95% identical to SEQ ID NO: 1.

EMBODIMENT 9

The method of any of embodiments 1-5, wherein SMN-NAT comprises a nucleic acid sequence 100% identical to SEQ ID NO: 1.

EMBODIMENT 10

The method of any one of embodiments 1-9, wherein the antisense compound comprises an oligonucleotide consisting of 12 to 30 linked nucleosides, and wherein the oligonucleotide is at least 85% complementary to a SMN-NAT nucleic acid sequence.

EMBODIMENT 11

The method of any of embodiments 1-9, wherein the oligonucleotide is at least 90% complementary over its entire length to an equal length region of a SMN-NAT nucleic acid sequence.

EMBODIMENT 12

The method of any of embodiments 1-9, wherein the oligonucleotide is at least 95% complementary over its entire length to an equal length region of a SMN-NAT nucleic acid sequence.

EMBODIMENT 13

The method of any of embodiments 1-9, wherein the oligonucleotide is 100% complementary over its entire length to an equal length region of a SMN-NAT nucleic acid sequence.

EMBODIMENT 14

The method of any one of embodiments 1-10, wherein the antisense compound or oligonucleotide is a single-stranded oligonucleotide.

EMBODIMENT 15

The method of any one of embodiments 10-14, wherein the oligonucleotide is a modified oligonucleotide.

EMBODIMENT 16

The method of any of embodiments 14-15, wherein the modified oligonucleotide consists of 10 to 30 linked nucleosides and has a nucleobase sequence comprising at least 8 contiguous nucleobases of any of the nucleobase sequences of SEQ ID NOs: 3, 7, 8, 9, 13, 17, 19, 20, 21, 22, 24, 25, 28, 31, 32, 34, 35, 39, 40, 41, 43, 44, 45, 51, 53, 56, 57, 58, 59, 62, 63, 64, 65, 66, 67, 68, 71, or 76.

EMBODIMENT 17

The method of any of embodiments 14-15, wherein the modified oligonucleotide consists of 10 to 30 linked nucleosides and has a nucleobase sequence comprising at least 10 contiguous nucleobases of any of the nucleobase sequences of SEQ ID NOs: 3, 7, 8, 9, 13, 17, 19, 20, 21, 22, 24, 25, 28, 31, 32, 34, 35, 39, 40, 41, 43, 44, 45, 51, 53, 56, 57, 58, 59, 62, 63, 64, 65, 66, 67, 68, 71, or 76.

EMBODIMENT 18

The method of any of embodiments 14-15, wherein the modified oligonucleotide consists of 10 to 30 linked nucleosides and has a nucleobase sequence comprising at least 12 contiguous nucleobases of any of the nucleobase sequences of SEQ ID NOs: 3, 7, 8, 9, 13, 17, 19, 20, 21, 22, 24, 25, 28, 31, 32, 34, 35, 39, 40, 41, 43, 44, 45, 51, 53, 56, 57, 58, 59, 62, 63, 64, 65, 66, 67, 68, 71, or 76.

EMBODIMENT 19

The method of any of embodiments 14-15, wherein the modified oligonucleotide consists of 10 to 30 linked nucleosides and has a nucleobase sequence comprising at least 14 contiguous nucleobases of any of the nucleobase sequences of SEQ ID NOs: 3, 7, 8, 9, 13, 17, 19, 20, 21, 22, 24, 25, 28, 31, 32, 34, 35, 39, 40, 41, 43, 44, 45, 51, 53, 56, 57, 58, 59, 62, 63, 64, 65, 66, 67, 68, 71, or 76.

EMBODIMENT 20

The method of any of embodiments 14-15, wherein the modified oligonucleotide consists of 10 to 30 linked nucleosides and has a nucleobase sequence comprising at least 15 contiguous nucleobases of any of the nucleobase sequences of SEQ ID NOs: 3, 7, 8, 9, 13, 17, 19, 20, 21, 22, 24, 25, 28, 31, 32, 34, 35, 39, 40, 41, 43, 44, 45, 51, 53, 56, 57, 58, 59, 62, 63, 64, 65, 66, 67, 68, 71, or 76.

EMBODIMENT 21

The method of any of embodiments 14-15, wherein the modified oligonucleotide consists of 10 to 30 linked nucleosides and has a nucleobase sequence comprising at least 16 contiguous nucleobases of any of the nucleobase sequences of SEQ ID NOs: 3, 7, 8, 9, 13, 17, 19, 20, 21, 22, 24, 25, 28, 31, 32, 34, 35, 39, 40, 41, 43, 44, 45, 51, 53, 56, 57, 58, 59, 62, 63, 64, 65, 66, 67, 68, 71, or 76.

EMBODIMENT 22

The method of any of embodiments 14-15, wherein the modified oligonucleotide consists of 10 to 30 linked nucleosides and has a nucleobase sequence comprising at least 17 contiguous nucleobases of any of the nucleobase sequences of SEQ ID NOs: 3, 7, 8, 9, 13, 17, 19, 20, 21, 22, 24, 25, 28, 31, 32, 34, 35, 39, 40, 41, 43, 44, 45, 51, 53, 56, 57, 58, 59, 62, 63, 64, 65, 66, 67, 68, 71, or 76.

EMBODIMENT 23

The method of any of embodiments 14-15, wherein the modified oligonucleotide consists of 10 to 30 linked nucleosides and has a nucleobase sequence comprising at least 18 contiguous nucleobases of any of the nucleobase sequences of SEQ ID NOs: 3, 7, 8, 9, 13, 17, 19, 20, 21, 22, 24, 25, 28, 31, 32, 34, 35, 39, 40, 41, 43, 44, 45, 51, 53, 56, 57, 58, 59, 62, 63, 64, 65, 66, 67, 68, 71, or 76.

EMBODIMENT 24

The method of any of embodiments 14-15, wherein the modified oligonucleotide has a nucleobase sequence selected from any one of SEQ ID NOs: 3, 7, 8, 9, 13, 17, 19, 20, 21, 22, 24, 25, 28, 31, 32, 34, 35, 39, 40, 41, 43, 44, 45, 51, 53, 56, 57, 58, 59, 62, 63, 64, 65, 66, 67, 68, 71, or 76.

EMBODIMENT 25

The method of any of embodiments 14 to 24, wherein the modified oligonucleotide is a gapmer.

EMBODIMENT 26

The method of any of embodiments 14 to 25, wherein the modified oligonucleotide consists of 20 linked nucleosides having a nucleobase sequence consisting of the sequence recited in SEQ ID NO: 3, 7, 8, 9, 13, 17, 19, 20, 21, 22, 24, 25, 28, 31, 32, 34, 35, 39, 40, 41, 43, 44, 45, 51, 53, 56, 57, 58, 59, 62, 63, 64, 65, 66, 67, 68, 71, or 76, wherein the modified oligonucleotide comprises:
  a gap segment consisting of linked deoxynucleosides;
  a 5' wing segment consisting of linked nucleosides; and
  a 3' wing segment consisting of linked nucleosides;
wherein the gap segment is positioned between the 5' wing segment and the 3' wing segment and wherein each nucleoside of each wing segment comprises a modified sugar.

EMBODIMENT 27

The method of any of embodiments 14 to 25, wherein the modified oligonucleotide consists of 20 linked nucleosides having a nucleobase sequence consisting of the sequence recited in SEQ ID NO: 3, 7, 8, 9, 13, 17, 19, 20, 21, 22, 24, 25, 28, 31, 32, 34, 35, 39, 40, 41, 43, 44, 45, 51, 53, 56, 57, 58, 59, 62, 63, 64, 65, 66, 67, 68, 71, or 76, wherein the modified oligonucleotide comprises:
  a gap segment consisting of ten linked deoxynucleosides;
    a 5' wing segment consisting of five linked nucleosides; and
    a 3' wing segment consisting of five linked nucleosides;
  wherein the gap segment is positioned between the 5' wing segment and the 3' wing segment, wherein each nucleoside of each wing segment comprises a 2'-O-methoxyethyl sugar; wherein each internucleoside linkage is a phosphorothioate linkage and wherein each cytosine is a 5-methylcytosine.

EMBODIMENT 28

The method of any of embodiments 12-24, wherein the modified oligonucleotide comprises at least one modified internucleoside linkage.

EMBODIMENT 29

The method of embodiment 28, wherein the modified internucleoside linkage is a phosphorothioate internucleoside linkage.

EMBODIMENT 30

The method of any of embodiments 12-24, wherein each internucloeoside linkage of the modified oligonucleotide is a modified internucleoside linkage.

EMBODIMENT 31

The method of embodiment 30, wherein the modified internucleoside linkage is a phosphorothioate internucleoside linkage.

EMBODIMENT 32

The method of any one of embodiments 12-31, wherein at least one nucleoside comprises a modified sugar.

EMBODIMENT 33

The method of embodiment 32, wherein the modified sugar is a bicyclic sugar comprising a bridge between the 4' and the 2' positions of the sugar.

EMBODIMENT 34

The method of embodiment 33, wherein the bridge is selected from 4'-CH(CH$_3$)—O-2', 4'-CH$_2$-2', 4'-(CH$_2$)$_2$-2', 4'-(CH$_2$)$_2$—O-2', 4'-CH$_2$—O—N(R$_1$)-2' and 4'-CH2-N(R$_1$)—O-2'- wherein each R1 is, independently, H, a protecting group or C1-C12 alkyl.

EMBODIMENT 35

The method of embodiment 34, wherein the bridge is 4'-CH(CH$_3$)—O-2'.

EMBODIMENT 36

The method of embodiment 34, wherein the bridge is selected from 4'-CH$_2$—O-2' and 4'-(CH$_2$)$_2$—O-2'.

EMBODIMENT 37

The method of embodiment 32, wherein the modified sugar comprises a 2'-O-methoxyethyl group.

EMBODIMENT 38

The method of any one of embodiments 12-37, wherein at least one nucleoside comprises a modified nucleobase.

EMBODIMENT 39

The method of embodiment 38, wherein the modified nucleobase is a 5-methylcytosine.

EMBODIMENT 40

The method of any one of embodiments 1-39, wherein the antisense compound or modified oligonucleotide increases expression of SMN by at least 20%.

EMBODIMENT 41

The method of any one of embodiments 1-39, wherein the antisense compound or modified oligonucleotide increases expression of SMN by at least 30%.

EMBODIMENT 42

The method of any one of embodiments 1-39, wherein the antisense compound or modified oligonucleotide increases expression of SMN by at least 40%.

EMBODIMENT 43

The method of any one of embodiments 1-39, wherein the antisense compound or modified oligonucleotide increases expression of SMN by at least 50%.

EMBODIMENT 44

The method of any one of embodiments 1-39, wherein the antisense compound or modified oligonucleotide increases expression of SMN by at least 60%.

EMBODIMENT 45

The method of any one of embodiments 1-39, wherein the antisense compound or modified oligonucleotide increases expression of SMN by at least 70%.

EMBODIMENT 46

The method of any one of embodiments 1-39, wherein the antisense compound or modified oligonucleotide increases expression of SMN by at least 80%.

EMBODIMENT 47

The method of any one of embodiments 1-39, wherein the antisense compound or modified oligonucleotide increases expression of SMN by at least 90%.

EMBODIMENT 48

The method of any one of embodiments 1-39, wherein the antisense compound or modified oligonucleotide increases expression of SMN by at least 100%.

EMBODIMENT 49

The method of any one of embodiments 1-39, wherein the antisense compound or modified oligonucleotide increases expression of SMN by at least 110%.

EMBODIMENT 50

The method of any one of embodiments 1-39, wherein the antisense compound or modified oligonucleotide increases expression of SMN by at least 120%.

EMBODIMENT 51

The method of any of embodiments 1-50, wherein the cell is in a subject.

EMBODIMENT 52

The method of any of embodiments 1-51, wherein the cell is in a subject.

EMBODIMENT 53

The method of embodiment 52, wherein the subject has one or more symptoms of SMA.

EMBODIMENT 54

A compound comprising a modified oligonucleotide consisting of 8 to 80 linked nucleosides having a nucleobase sequence comprising a portion of at least 8 contiguous nucleobases 100% complementary to an equal length portion of a SMN-NAT transcript.

EMBODIMENT 55

A compound comprising a modified oligonucleotide consisting of 8 to 80 linked nucleosides having a nucleobase sequence comprising a portion of at least 8 contiguous nucleobases 100% complementary to an equal length portion of SEQ ID NO. 1.

EMBODIMENT 56

A compound comprising a modified oligonucleotide consisting of 8 to 80 linked nucleosides having a nucleobase sequence comprising any one of SEQ ID NO: SEQ ID NO: 3, 7, 8, 9, 13, 17, 19, 20, 21, 22, 24, 25, 28, 31, 32, 34, 35, 39, 40, 41, 43, 44, 45, 51, 53, 56, 57, 58, 59, 62, 63, 64, 65, 66, 67, 68, 71, or 76

EMBODIMENT 57

A compound comprising a modified oligonucleotide having a nucleobase sequence consisting of any one of SEQ ID NO: SEQ ID NO: 3, 7, 8, 9, 13, 17, 19, 20, 21, 22, 24, 25, 28, 31, 32, 34, 35, 39, 40, 41, 43, 44, 45, 51, 53, 56, 57, 58, 59, 62, 63, 64, 65, 66, 67, 68, 71, or 76

EMBODIMENT 58

A compound comprising a modified oligonucleotide consisting of 10 to 30 linked nucleosides and having a nucleobase sequence comprising at least 8 contiguous nucleobases of any of the nucleobase sequences of SEQ ID NOs: 3, 7, 8, 9, 13, 17, 19, 20, 21, 22, 24, 25, 28, 31, 32, 34, 35, 39, 40, 41, 43, 44, 45, 51, 53, 56, 57, 58, 59, 62, 63, 64, 65, 66, 67, 68, 71, or 76.

EMBODIMENT 59

A compound comprising a modified oligonucleotide consisting of 10 to 30 linked nucleosides and having a nucleobase sequence comprising at least 9 contiguous nucleobases of any of the nucleobase sequences of SEQ ID NOs: 3, 7, 8, 9, 13, 17, 19, 20, 21, 22, 24, 25, 28, 31, 32, 34, 35, 39, 40, 41, 43, 44, 45, 51, 53, 56, 57, 58, 59, 62, 63, 64, 65, 66, 67, 68, 71, or 76.

EMBODIMENT 60

A compound comprising a modified oligonucleotide consisting of 10 to 30 linked nucleosides and having a nucleobase sequence comprising at least 10 contiguous nucleobases of any of the nucleobase sequences of SEQ ID NOs: 3, 7, 8, 9, 13, 17, 19, 20, 21, 22, 24, 25, 28, 31, 32, 34, 35, 39, 40, 41, 43, 44, 45, 51, 53, 56, 57, 58, 59, 62, 63, 64, 65, 66, 67, 68, 71, or 76.

EMBODIMENT 61

A compound comprising a modified oligonucleotide consisting of 10 to 30 linked nucleosides and having a nucleobase sequence comprising at least 11 contiguous nucleobases of any of the nucleobase sequences of SEQ ID NOs: 3, 7, 8, 9, 13, 17, 19, 20, 21, 22, 24, 25, 28, 31, 32, 34, 35, 39, 40, 41, 43, 44, 45, 51, 53, 56, 57, 58, 59, 62, 63, 64, 65, 66, 67, 68, 71, or 76.

EMBODIMENT 62

A compound comprising a modified oligonucleotide consisting of 10 to 30 linked nucleosides and having a nucleobase sequence comprising at least 12 contiguous nucleobases of any of the nucleobase sequences of SEQ ID NOs:

3, 7, 8, 9, 13, 17, 19, 20, 21, 22, 24, 25, 28, 31, 32, 34, 35, 39, 40, 41, 43, 44, 45, 51, 53, 56, 57, 58, 59, 62, 63, 64, 65, 66, 67, 68, 71, or 76.

EMBODIMENT 63

A compound comprising a modified oligonucleotide consisting of 10 to 30 linked nucleosides and having a nucleobase sequence comprising at least 14 contiguous nucleobases of any of the nucleobase sequences of SEQ ID NOs: 3, 7, 8, 9, 13, 17, 19, 20, 21, 22, 24, 25, 28, 31, 32, 34, 35, 39, 40, 41, 43, 44, 45, 51, 53, 56, 57, 58, 59, 62, 63, 64, 65, 66, 67, 68, 71, or 76.

EMBODIMENT 64

A compound comprising a modified oligonucleotide consisting of 10 to 30 linked nucleosides and having a nucleobase sequence comprising at least 15 contiguous nucleobases of any of the nucleobase sequences of SEQ ID NOs: 3, 7, 8, 9, 13, 17, 19, 20, 21, 22, 24, 25, 28, 31, 32, 34, 35, 39, 40, 41, 43, 44, 45, 51, 53, 56, 57, 58, 59, 62, 63, 64, 65, 66, 67, 68, 71, or 76.

EMBODIMENT 65

A compound comprising a modified oligonucleotide consisting of 10 to 30 linked nucleosides and having a nucleobase sequence comprising at least 16 contiguous nucleobases of any of the nucleobase sequences of SEQ ID NOs: 3, 7, 8, 9, 13, 17, 19, 20, 21, 22, 24, 25, 28, 31, 32, 34, 35, 39, 40, 41, 43, 44, 45, 51, 53, 56, 57, 58, 59, 62, 63, 64, 65, 66, 67, 68, 71, or 76.

EMBODIMENT 66

A compound comprising a modified oligonucleotide consisting of 10 to 30 linked nucleosides and having a nucleobase sequence comprising at least 17 contiguous nucleobases of any of the nucleobase sequences of SEQ ID NOs: 3, 7, 8, 9, 13, 17, 19, 20, 21, 22, 24, 25, 28, 31, 32, 34, 35, 39, 40, 41, 43, 44, 45, 51, 53, 56, 57, 58, 59, 62, 63, 64, 65, 66, 67, 68, 71, or 76.

EMBODIMENT 67

A compound comprising a modified oligonucleotide consisting of 10 to 30 linked nucleosides and having a nucleobase sequence comprising at least 18 contiguous nucleobases of any of the nucleobase sequences of SEQ ID NOs: 3, 7, 8, 9, 13, 17, 19, 20, 21, 22, 24, 25, 28, 31, 32, 34, 35, 39, 40, 41, 43, 44, 45, 51, 53, 56, 57, 58, 59, 62, 63, 64, 65, 66, 67, 68, 71, or 76.

EMBODIMENT 68

A compound comprising a modified oligonucleotide consisting of 10 to 30 linked nucleosides and having a nucleobase sequence comprising the nucleobase sequence of any one of SEQ ID NOs: 3, 7, 8, 9, 13, 17, 19, 20, 21, 22, 24, 25, 28, 31, 32, 34, 35, 39, 40, 41, 43, 44, 45, 51, 53, 56, 57, 58, 59, 62, 63, 64, 65, 66, 67, 68, 71, or 76.

EMBODIMENT 69

A compound comprising a modified oligonucleotide consisting of the nucleobase sequence of any one of SEQ ID NOs: 3, 7, 8, 9, 13, 17, 19, 20, 21, 22, 24, 25, 28, 31, 32, 34, 35, 39, 40, 41, 43, 44, 45, 51, 53, 56, 57, 58, 59, 62, 63, 64, 65, 66, 67, 68, 71, or 76.

EMBODIMENT 70

A compound comprising a modified oligonucleotide consisting of 10 to 30 linked nucleosides having a nucleobase sequence comprising any one of SEQ ID NOs: 3, 7, 8, 9, 13, 17, 19, 20, 21, 22, 24, 25, 28, 31, 32, 34, 35, 39, 40, 41, 43, 44, 45, 51, 53, 56, 57, 58, 59, 62, 63, 64, 65, 66, 67, 68, 71, or 76, wherein the modified oligonucleotide comprises:
a gap segment consisting of linked deoxynucleosides;
a 5' wing segment consisting of linked nucleosides; and
a 3' wing segment consisting of linked nucleosides;
wherein the gap segment is positioned between the 5' wing segment and the 3' wing segment and wherein each nucleoside of each wing segment comprises a modified sugar.

EMBODIMENT 71

A compound comprising a modified oligonucleotide consisting of 20 linked nucleosides having a nucleobase sequence consisting of the sequence recited in SEQ ID NOs: 3, 7, 8, 9, 13, 17, 19, 20, 21, 22, 24, 25, 28, 31, 32, 34, 35, 39, 40, 41, 43, 44, 45, 51, 53, 56, 57, 58, 59, 62, 63, 64, 65, 66, 67, 68, 71, or 76, wherein the modified oligonucleotide comprises
a gap segment consisting of ten linked deoxynucleosides;
a 5' wing segment consisting of five linked nucleosides; and
a 3' wing segment consisting of five linked nucleosides;
wherein the gap segment is positioned between the 5' wing segment and the 3' wing segment, wherein each nucleoside of each wing segment comprises a 2'-O-methoxyethyl sugar; wherein each internucleoside linkage is a phosphorothioate linkage and wherein each cytosine is a 5-methylcytosine.

EMBODIMENT 72

A compound comprising a modified oligonucleotide consisting of 20 linked nucleosides having a nucleobase sequence consisting of the sequence recited in SEQ ID NO: 59, wherein the modified oligonucleotide comprises
a gap segment consisting of ten linked deoxynucleosides;
a 5' wing segment consisting of five linked nucleosides; and
a 3' wing segment consisting of five linked nucleosides;
wherein the gap segment is positioned between the 5' wing segment and the 3' wing segment, wherein each nucleoside of each wing segment comprises a 2'-O-methoxyethyl sugar; wherein each internucleoside linkage is a phosphorothioate linkage and wherein each cytosine is a 5-methylcytosine.

EMBODIMENT 73

A compound comprising a modified oligonucleotide consisting of 20 linked nucleosides having a nucleobase sequence consisting of the sequence recited in SEQ ID NO: 64, wherein the modified oligonucleotide comprises
a gap segment consisting of ten linked deoxynucleosides;
a 5' wing segment consisting of five linked nucleosides; and
a 3' wing segment consisting of five linked nucleosides;

wherein the gap segment is positioned between the 5' wing segment and the 3' wing segment, wherein each nucleoside of each wing segment comprises a 2'-O-methoxyethyl sugar; wherein each internucleoside linkage is a phosphorothioate linkage and wherein each cytosine is a 5-methylcytosine.

EMBODIMENT 74

The compound of any one of embodiments 54-73, wherein the modified oligonucleotide comprises at least one modified internucleoside linkage, at least one modified sugar, or at least one modified nucleobase.

EMBODIMENT 75

The compound of embodiment 74, wherein the modified internucleoside linkage is a phosphorothioate internucleoside linkage.

EMBODIMENT 76

The compound of any one of embodiments 54-73, wherein each internucleoside linkage of the modified oligonucleotide comprises at least one modified internucleoside linkage.

EMBODIMENT 77

The compound of embodiment 76, wherein the modified internucleoside linkage is a phosphorothioate internucleoside linkage.

EMBODIMENT 78

The compound of any of embodiments 74-77, wherein the modified sugar is a bicyclic sugar.

EMBODIMENT 79

The compound of embodiment 78, wherein the bicyclic sugar is selected from the group consisting of: 4'-(CH$_2$)—O-2' (LNA); 4'-(CH$_2$)$_2$—O-2' (ENA); and 4'-CH(CH$_3$)—O-2' (cEt).

EMBODIMENT 80

The compound of any of embodiments 74-77, wherein the modified sugar is 2'-O-methoxyethyl.

EMBODIMENT 81

The compound of any one of embodiments 74-81, wherein the modified nucleobase is a 5-methylcytosine.

EMBODIMENT 82

The compound of any one of embodiments 54-81, wherein the modified oligonucleotide comprises:
(a) a gap segment consisting of linked deoxynucleosides;
(b) a 5' wing segment consisting of linked nucleosides; and
(c) a 3' wing segment consisting of linked nucleosides;
wherein the gap segment is positioned immediately adjacent to and between the 5' wing segment and the 3' wing segment and wherein each nucleoside of each wing segment comprises a modified sugar.

EMBODIMENT 83

The compound of any one of embodiments 54-82, wherein the compound is single-stranded.

EMBODIMENT 84

The compound of any one of embodiments 54-82, wherein the compound is double-stranded.

EMBODIMENT 85

The compound of any one of embodiments 54-84, wherein the modified oligonucleotide consists of 10 to 30 linked nucleosides.

EMBODIMENT 86

The compound of any one of embodiments 54-84, wherein the modified oligonucleotide consists of 12 to 30 linked nucleosides.

EMBODIMENT 87

The compound of any one of embodiments 54-84, wherein the modified oligonucleotide consists of 15 to 30 linked nucleosides.

EMBODIMENT 88

A composition comprising the compound of any one of embodiments 54-87 or salt thereof and a pharmaceutically acceptable carrier.

EMBODIMENT 89

A method of reducing expression of SMN-NAT in a cell, comprising contacting a cell with the compound or composition of any of embodiments 54-88.

EMBODIMENT 90

The method of embodiment 89, wherein the cell is in vitro.

EMBODIMENT 91

The method of embodiment 89, wherein the cell is in an animal.

EMBODIMENT 92

A method of increasing expression of SMN in a cell, comprising contacting a cell with the compound or composition of any of embodiments 54-88.

EMBODIMENT 93

The method of embodiment 92, wherein the SMN is mRNA.

EMBODIMENT 94

The method of embodiment 92, wherein the SMN is pre-mRNA.

EMBODIMENT 95

The method of embodiment 92, wherein the SMN is protein.

EMBODIMENT 96

The method of any of embodiments 93-95, wherein the SMN is SMN2.

EMBODIMENT 97

The method of any of embodiments 92-96, wherein the cell is in vitro.

EMBODIMENT 98

The method of any of embodiments 92-96, wherein the cell is in an animal.

DETAILED DESCRIPTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference for the portions of the document discussed herein, as well as in their entirety.

It is understood that the sequence set forth in each SEQ ID NO described herein is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by Isis Number (Isis No) indicate a combination of nucleobase sequence and motif.

Unless specific definitions are provided, the nomenclature used in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Certain such techniques and procedures may be found for example in "Carbohydrate Modifications in Antisense Research" Edited by Sangvi and Cook, American Chemical Society, Washington D.C., 1994; "Remington's Pharmaceutical Sciences," Mack Publishing Co., Easton, Pa., 21$^{st}$ edition, 2005; and "Antisense Drug Technology, Principles, Strategies, and Applications" Edited by Stanley T. Crooke, CRC Press, Boca Raton, Fla.; and Sambrook et al., "Molecular Cloning, A laboratory Manual," 2$^{nd}$ Edition, Cold Spring Harbor Laboratory Press, 1989, which are hereby incorporated by reference for any purpose.

Where permitted, all patents, applications, published applications and other publications and other data referred to throughout in the disclosure are incorporated by reference herein in their entirety.

Unless otherwise indicated, the following terms have the following meanings:

As used herein, "SMN-NAT" means a natural antisense transcript of SMN. In certain embodiments, SMN-NAT transcript comprises GenBank accession # BC045789.1 (SEQ ID NO. 1).

As used herein, "Survival of Motor Neuron (SMN)" means any SMN nucleic acid or protein. "SMN nucleic acid" means any nucleic acid encoding SMN. For example, in certain embodiments, a SMN nucleic acid includes a DNA sequence encoding SMN, an RNA sequence transcribed from DNA encoding SMN, including a non-protein encoding (i.e. non-coding) RNA sequence, and an mRNA sequence encoding SMN. "SMN mRNA" means an mRNA encoding a SMN protein.

As used herein, "nucleoside" means a compound comprising a nucleobase moiety and a sugar moiety. Nucleosides include, but are not limited to, naturally occurring nucleosides (as found in DNA and RNA) and modified nucleosides. Nucleosides may be linked to a phosphate moiety.

As used herein, "chemical modification" means a chemical difference in a compound when compared to a naturally occurring counterpart. In reference to an oligonucleotide, chemical modification does not include differences only in nucleobase sequence. Chemical modifications of oligonucleotides include nucleoside modifications (including sugar moiety modifications and nucleobase modifications) and internucleoside linkage modifications.

As used herein, "furanosyl" means a structure comprising a 5-membered ring comprising four carbon atoms and one oxygen atom.

As used herein, "naturally occurring sugar moiety" means a ribofuranosyl as found in naturally occurring RNA or a deoxyribofuranosyl as found in naturally occurring DNA.

As used herein, "sugar moiety" means a naturally occurring sugar moiety or a modified sugar moiety of a nucleoside.

As used herein, "modified sugar moiety" means a substituted sugar moiety, a bicyclic or tricyclic sugar moiety, or a sugar surrogate.

As used herein, "substituted sugar moiety" means a furanosyl comprising at least one substituent group that differs from that of a naturally occurring sugar moiety. Substituted sugar moieties include, but are not limited to furanosyls comprising substituents at the 2'-position, the 3'-position, the 5'-position and/or the 4'-position.

As used herein, "2'-substituted sugar moiety" means a furanosyl comprising a substituent at the 2'-position other than H or OH. Unless otherwise indicated, a 2'-substituted sugar moiety is not a bicyclic sugar moiety (i.e., the 2'-substituent of a 2'-substituted sugar moiety does not form a bridge to another atom of the furanosyl ring.

As used herein, "MOE" means —OCH$_2$CH$_2$OCH$_3$.

As used herein, "bicyclic sugar moiety" means a modified sugar moiety comprising a 4 to 7 membered ring (including but not limited to a furanosyl) comprising a bridge connecting two atoms of the 4 to 7 membered ring to form a second ring, resulting in a bicyclic structure. In certain embodiments, the 4 to 7 membered ring is a sugar ring. In certain embodiments the 4 to 7 membered ring is a furanosyl. In certain such embodiments, the bridge connects the 2'-carbon and the 4'-carbon of the furanosyl.

As used herein the term "sugar surrogate" means a structure that does not comprise a furanosyl and that is capable of replacing the naturally occurring sugar moiety of a nucleoside, such that the resulting nucleoside is capable of (1) incorporation into an oligonucleotide and (2) hybridization to a complementary nucleoside. Such structures include rings comprising a different number of atoms than furanosyl (e.g., 4, 6, or 7-membered rings); replacement of the oxygen of a furanosyl with a non-oxygen atom (e.g., carbon, sulfur, or nitrogen); or both a change in the number of atoms and a replacement of the oxygen. Such structures may also comprise substitutions corresponding to those described for substituted sugar moieties (e.g., 6-membered carbocyclic bicyclic sugar surrogates optionally comprising additional substituents). Sugar surrogates also include more complex sugar replacements (e.g., the non-ring systems of peptide nucleic acid). Sugar surrogates include without limitation morpholino, modified morpholinos, cyclohexenyls and cyclohexitols.

As used herein, "nucleotide" means a nucleoside further comprising a phosphate linking group. As used herein, "linked nucleosides" may or may not be linked by phosphate linkages and thus includes, but is not limited to "linked nucleotides." As used herein, "linked nucleosides" are nucleosides that are connected in a continuous sequence (i.e. no additional nucleosides are present between those that are linked).

As used herein, "nucleobase" means a group of atoms that can be linked to a sugar moiety to create a nucleoside that is capable of incorporation into an oligonucleotide, and wherein the group of atoms is capable of bonding with a complementary naturally occurring nucleobase of another oligonucleotide or nucleic acid. Nucleobases may be naturally occurring or may be modified.

As used herein, "heterocyclic base" or "heterocyclic nucleobase" means a nucleobase comprising a heterocyclic structure.

As used herein the terms, "unmodified nucleobase" or "naturally occurring nucleobase" means the naturally occurring heterocyclic nucleobases of RNA or DNA: the purine bases adenine (A) and guanine (G), and the pyrimidine bases thymine (T), cytosine (C) (including 5-methyl C), and uracil (U).

As used herein, "modified nucleobase" means any nucleobase that is not a naturally occurring nucleobase.

As used herein, "modified nucleoside" means a nucleoside comprising at least one chemical modification compared to naturally occurring RNA or DNA nucleosides. Modified nucleosides comprise a modified sugar moiety and/or a modified nucleobase.

As used herein, "bicyclic nucleoside" or "BNA" means a nucleoside comprising a bicyclic sugar moiety.

As used herein, "constrained ethyl nucleoside" or "cEt" means a nucleoside comprising a bicyclic sugar moiety comprising a 4'-CH(CH$_3$)—O-2'bridge.

As used herein, "locked nucleic acid nucleoside" or "LNA" means a nucleoside comprising a bicyclic sugar moiety comprising a 4'-CH$_2$—O-2'bridge.

As used herein, "2'-substituted nucleoside" means a nucleoside comprising a substituent at the 2'-position other than H or OH. Unless otherwise indicated, a 2'-substituted nucleoside is not a bicyclic nucleoside.

As used herein, "2'-deoxynucleoside" means a nucleoside comprising 2'-H furanosyl sugar moiety, as found in naturally occurring deoxyribonucleosides (DNA). In certain embodiments, a 2'-deoxynucleoside may comprise a modified nucleobase or may comprise an RNA nucleobase (e.g., uracil).

As used herein, "oligonucleotide" means a compound comprising a plurality of linked nucleosides. In certain embodiments, an oligonucleotide comprises one or more unmodified ribonucleosides (RNA) and/or unmodified deoxyribonucleosides (DNA) and/or one or more modified nucleosides.

As used herein "oligonucleoside" means an oligonucleotide in which none of the internucleoside linkages contains a phosphorus atom. As used herein, oligonucleotides include oligonucleosides.

As used herein, "modified oligonucleotide" means an oligonucleotide comprising at least one modified nucleoside and/or at least one modified internucleoside linkage.

As used herein "internucleoside linkage" means a covalent linkage between adjacent nucleosides in an oligonucleotide.

As used herein "naturally occurring internucleoside linkage" means a 3' to 5' phosphodiester linkage.

As used herein, "modified internucleoside linkage" means any internucleoside linkage other than a naturally occurring internucleoside linkage.

As used herein, "oligomeric compound" means a polymeric structure comprising two or more sub-structures. In certain embodiments, an oligomeric compound comprises an oligonucleotide. In certain embodiments, an oligomeric compound comprises one or more conjugate groups and/or terminal groups. In certain embodiments, an oligomeric compound consists of an oligonucleotide.

As used herein, "terminal group" means one or more atom attached to either, or both, the 3' end or the 5' end of an oligonucleotide. In certain embodiments a terminal group is a conjugate group. In certain embodiments, a terminal group comprises one or more terminal group nucleosides.

As used herein, "conjugate" means an atom or group of atoms bound to an oligonucleotide or oligomeric compound. In general, conjugate groups modify one or more properties of the compound to which they are attached, including, but not limited to pharmacodynamic, pharmacokinetic, binding, absorption, cellular distribution, cellular uptake, charge and/or clearance properties.

As used herein, "conjugate linking group" means any atom or group of atoms used to attach a conjugate to an oligonucleotide or oligomeric compound.

As used herein, "antisense compound" means a compound comprising or consisting of an oligonucleotide at least a portion of which is complementary to a target nucleic acid to which it is capable of hybridizing, resulting in at least one antisense activity.

As used herein, "antisense activity" means any detectable and/or measurable change attributable to the hybridization of an antisense compound to its target nucleic acid.

As used herein, "detecting" or "measuring" means that a test or assay for detecting or measuring is performed. Such detection and/or measuring may result in a value of zero. Thus, if a test for detection or measuring results in a finding of no activity (activity of zero), the step of detecting or measuring the activity has nevertheless been performed.

As used herein, "detectable and/or measureable activity" means a statistically significant activity that is not zero.

As used herein, "essentially unchanged" means little or no change in a particular parameter, particularly relative to another parameter which changes much more. In certain embodiments, a parameter is essentially unchanged when it changes less than 5%. In certain embodiments, a parameter is essentially unchanged if it changes less than two-fold while another parameter changes at least ten-fold. For example, in certain embodiments, an antisense activity is a change in the amount of a target nucleic acid. In certain such embodiments, the amount of a non-target nucleic acid is essentially unchanged if it changes much less than the target nucleic acid does, but the change need not be zero.

As used herein, "expression" means the process by which a gene ultimately results in a protein. Expression includes, but is not limited to, transcription, post-transcriptional modification (e.g., splicing, polyadenlyation, addition of 5'-cap), and translation.

As used herein, "target nucleic acid" means a nucleic acid molecule to which an antisense compound hybridizes.

As used herein, "mRNA" means an RNA molecule that encodes a protein.

As used herein, "pre-mRNA" means an RNA transcript that has not been fully processed into mRNA. Pre-mRNA includes one or more intron.

As used herein, "transcript" means an RNA molecule transcribed from DNA. Transcripts include, but are not limited to mRNA, pre-mRNA, and partially processed RNA.

As used herein, "targeting" or "targeted to" means the association of an antisense compound to a particular target nucleic acid molecule or a particular region of a target nucleic acid molecule. An antisense compound targets a target nucleic acid if it is sufficiently complementary to the target nucleic acid to allow hybridization under physiological conditions.

As used herein, "nucleobase complementarity" or "complementarity" when in reference to nucleobases means a nucleobase that is capable of base pairing with another nucleobase. For example, in DNA, adenine (A) is complementary to thymine (T). For example, in RNA, adenine (A) is complementary to uracil (U). In certain embodiments, complementary nucleobase means a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair. Nucleobases comprising certain modifications may maintain the ability to pair with a counterpart nucleobase and thus, are still capable of nucleobase complementarity.

As used herein, "non-complementary" in reference to nucleobases means a pair of nucleobases that do not form hydrogen bonds with one another.

As used herein, "complementary" in reference to oligomeric compounds (e.g., linked nucleosides, oligonucleotides, or nucleic acids) means the capacity of such oligomeric compounds or regions thereof to hybridize to another oligomeric compound or region thereof through nucleobase complementarity under stringent conditions. Complementary oligomeric compounds need not have nucleobase complementarity at each nucleoside. Rather, some mismatches are tolerated. In certain embodiments, complementary oligomeric compounds or regions are complementary at 70% of the nucleobases (70% complementary). In certain embodiments, complementary oligomeric compounds or regions are 80% complementary. In certain embodiments, complementary oligomeric compounds or regions are 90% complementary. In certain embodiments, complementary oligomeric compounds or regions are 95% complementary. In certain embodiments, complementary oligomeric compounds or regions are 100% complementary.

As used herein, "hybridization" means the pairing of complementary oligomeric compounds (e.g., an antisense compound and its target nucleic acid). While not limited to a particular mechanism, the most common mechanism of pairing involves hydrogen bonding, which may be Watson-Crick, Hoogsteen or reversed Hoogsteen hydrogen bonding, between complementary nucleobases.

As used herein, "specifically hybridizes" means the ability of an oligomeric compound to hybridize to one nucleic acid site with greater affinity than it hybridizes to another nucleic acid site. In certain embodiments, an antisense oligonucleotide specifically hybridizes to more than one target site.

As used herein, "percent complementarity" means the percentage of nucleobases of an oligomeric compound that are complementary to an equal-length portion of a target nucleic acid. Percent complementarity is calculated by dividing the number of nucleobases of the oligomeric compound that are complementary to nucleobases at corresponding positions in the target nucleic acid by the total length of the oligomeric compound.

As used herein, "percent identity" means the number of nucleobases in a first nucleic acid that are the same type (independent of chemical modification) as nucleobases at corresponding positions in a second nucleic acid, divided by the total number of nucleobases in the first nucleic acid.

As used herein, "modulation" means a change of amount or quality of a molecule, function, or activity when compared to the amount or quality of a molecule, function, or activity prior to modulation. For example, modulation includes the change, either an increase (stimulation or induction) or a decrease (inhibition or reduction) in gene expression. As a further example, modulation of expression can include a change in splice site selection of pre-mRNA processing, resulting in a change in the absolute or relative amount of a particular splice-variant compared to the amount in the absence of modulation.

As used herein, "motif" means a pattern of chemical modifications in an oligomeric compound or a region thereof. Motifs may be defined by modifications at certain nucleosides and/or at certain linking groups of an oligomeric compound.

As used herein, "nucleoside motif" means a pattern of nucleoside modifications in an oligomeric compound or a region thereof. The linkages of such an oligomeric compound may be modified or unmodified. Unless otherwise indicated, motifs herein describing only nucleosides are intended to be nucleoside motifs. Thus, in such instances, the linkages are not limited.

As used herein, "sugar motif" means a pattern of sugar modifications in an oligomeric compound or a region thereof.

As used herein, "linkage motif" means a pattern of linkage modifications in an oligomeric compound or region thereof. The nucleosides of such an oligomeric compound may be modified or unmodified. Unless otherwise indicated, motifs herein describing only linkages are intended to be linkage motifs. Thus, in such instances, the nucleosides are not limited.

As used herein, "nucleobase modification motif" means a pattern of modifications to nucleobases along an oligonucleotide. Unless otherwise indicated, a nucleobase modification motif is independent of the nucleobase sequence.

As used herein, "sequence motif" means a pattern of nucleobases arranged along an oligonucleotide or portion thereof. Unless otherwise indicated, a sequence motif is independent of chemical modifications and thus may have any combination of chemical modifications, including no chemical modifications.

As used herein, "type of modification" in reference to a nucleoside or a nucleoside of a "type" means the chemical modification of a nucleoside and includes modified and unmodified nucleosides. Accordingly, unless otherwise indicated, a "nucleoside having a modification of a first type" may be an unmodified nucleoside.

As used herein, "differently modified" mean chemical modifications or chemical substituents that are different from one another, including absence of modifications. Thus, for example, a MOE nucleoside and an unmodified DNA nucleoside are "differently modified," even though the DNA nucleoside is unmodified. Likewise, DNA and RNA are "differently modified," even though both are naturally-occurring unmodified nucleosides. Nucleosides that are the same but for comprising different nucleobases are not differently modified. For example, a nucleoside comprising a 2'-OMe modified sugar and an unmodified adenine nucleobase and a nucleoside comprising a 2'-OMe modified sugar and an unmodified thymine nucleobase are not differently modified.

As used herein, "the same type of modifications" refers to modifications that are the same as one another, including absence of modifications. Thus, for example, two unmodified DNA nucleoside have "the same type of modification," even though the DNA nucleoside is unmodified. Such nucleosides having the same type modification may comprise different nucleobases.

As used herein, "pharmaceutically acceptable carrier or diluent" means any substance suitable for use in administering to an animal. In certain embodiments, a pharmaceutically acceptable carrier or diluent is sterile saline. In certain embodiments, such sterile saline is pharmaceutical grade saline.

As used herein, "substituent" and "substituent group," means an atom or group that replaces the atom or group of a named parent compound. For example a substituent of a modified nucleoside is any atom or group that differs from the atom or group found in a naturally occurring nucleoside (e.g., a modified 2'-substituent is any atom or group at the 2'-position of a nucleoside other than H or OH). Substituent groups can be protected or unprotected. In certain embodiments, compounds of the present invention have substituents at one or at more than one position of the parent compound. Substituents may also be further substituted with other substituent groups and may be attached directly or via a linking group such as an alkyl or hydrocarbyl group to a parent compound.

Likewise, as used herein, "substituent" in reference to a chemical functional group means an atom or group of atoms differs from the atom or a group of atoms normally present in the named functional group. In certain embodiments, a substituent replaces a hydrogen atom of the functional group (e.g., in certain embodiments, the substituent of a substituted methyl group is an atom or group other than hydrogen which replaces one of the hydrogen atoms of an unsubstituted methyl group). Unless otherwise indicated, groups amenable for use as substituents include without limitation, halogen, hydroxyl, alkyl, alkenyl, alkynyl, acyl (—C(O)$R_{aa}$), carboxyl (—C(O)O—$R_{aa}$), aliphatic groups, alicyclic groups, alkoxy, substituted oxy (—O—$R_{aa}$), aryl, aralkyl, heterocyclic radical, heteroaryl, heteroarylalkyl, amino (—N($R_{bb}$)— ($R_{cc}$)), imino(=N$R_{bb}$), amido (—C(O)N($R_{bb}$)($R_{cc}$) or —N($R_{bb}$)C(O)$R_{aa}$), azido (—$N_3$), nitro (—$NO_2$), cyano (—CN), carbamido (—OC(O)N($R_{bb}$)($R_{cc}$) or —N($R_{bb}$)C(O)O$R_{aa}$), ureido (—N($R_{bb}$)C(O)N($R_{bb}$)($R_{cc}$)), thioureido (—N($R_{bb}$)C(S)N($R_{bb}$)($R_{cc}$)), guanidinyl (—N($R_{bb}$)C(=N$R_{bb}$)N($R_{bb}$)($R_{cc}$)), amidinyl (—C(=N$R_{bb}$)N($R_{bb}$)($R_{cc}$) or —N($R_{bb}$)C(=N$R_{bb}$)($R_{aa}$)), thiol (—S$R_{bb}$), sulfinyl (—S(O)$R_{bb}$), sulfonyl (—S(O)$_2R_{bb}$) and sulfonamidyl (—S(O)$_2$N($R_{bb}$)($R_{cc}$) or —N($R_{bb}$)S(O)$_2R_{bb}$). Wherein each $R_{aa}$, $R_{bb}$ and $R_{cc}$ is, independently, H, an optionally linked chemical functional group or a further substituent group with a preferred list including without limitation, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

As used herein, "alkyl," as used herein, means a saturated straight or branched hydrocarbon radical containing up to twenty four carbon atoms. Examples of alkyl groups include without limitation, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred.

As used herein, "alkenyl," means a straight or branched hydrocarbon chain radical containing up to twenty four carbon atoms and having at least one carbon-carbon double bond. Examples of alkenyl groups include without limitation, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

As used herein, "alkynyl," means a straight or branched hydrocarbon radical containing up to twenty four carbon atoms and having at least one carbon-carbon triple bond. Examples of alkynyl groups include, without limitation, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

As used herein, "acyl," means a radical formed by removal of a hydroxyl group from an organic acid and has the general Formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

As used herein, "alicyclic" means a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups.

As used herein, "aliphatic" means a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation, polyalkoxys, such as polyalkylene glycols, polyamines, and polyimines. Aliphatic groups as used herein may optionally include further substituent groups.

As used herein, "alkoxy" means a radical formed between an alkyl group and an oxygen atom wherein the oxygen atom is used to attach the alkoxy group to a parent molecule. Examples of alkoxy groups include without limitation, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

As used herein, "aminoalkyl" means an amino substituted $C_1$-$C_{12}$ alkyl radical. The alkyl portion of the radical forms a covalent bond with a parent molecule. The amino group can be located at any position and the aminoalkyl group can be substituted with a further substituent group at the alkyl and/or amino portions.

As used herein, "aralkyl" and "arylalkyl" mean an aromatic group that is covalently linked to a $C_1$-$C_{12}$ alkyl radical. The alkyl radical portion of the resulting aralkyl (or arylalkyl) group forms a covalent bond with a parent molecule. Examples include without limitation, benzyl, phenethyl and the like. Aralkyl groups as used herein may optionally include further substituent groups attached to the alkyl, the aryl or both groups that form the radical group.

As used herein, "aryl" and "aromatic" mean a mono- or polycyclic carbocyclic ring system radicals having one or more aromatic rings. Examples of aryl groups include without limitation, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

As used herein, "halo" and "halogen," mean an atom selected from fluorine, chlorine, bromine and iodine.

As used herein, "heteroaryl," and "heteroaromatic," mean a radical comprising a mono- or poly-cyclic aromatic ring, ring system or fused ring system wherein at least one of the rings is aromatic and includes one or more heteroatoms. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include without limitation, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl and the like. Heteroaryl radicals can be attached to a parent molecule directly or through a linking moiety such as an aliphatic group or hetero atom. Heteroaryl groups as used herein may optionally include further substituent groups.

Oligomeric Compounds

In certain embodiments, the present invention provides oligomeric compounds. In certain embodiments, such oligomeric compounds comprise oligonucleotides optionally comprising one or more conjugate and/or terminal groups. In certain embodiments, an oligomeric compound consists of an oligonucleotide. In certain embodiments, oligonucleotides comprise one or more chemical modifications. Such chemical modifications include modifications one or more nucleoside (including modifications to the sugar moiety and/or the nucleobase) and/or modifications to one or more internucleoside linkage.

Certain Sugar Moieties

In certain embodiments, oligomeric compounds of the invention comprise one or more modified nucleosides comprising a modified sugar moiety. Such oligomeric compounds comprising one or more sugar-modified nucleosides may have desirable properties, such as enhanced nuclease stability or increased binding affinity with a target nucleic acid relative to oligomeric compounds comprising only nucleosides comprising naturally occurring sugar moieties. In certain embodiments, modified sugar moieties are substituted sugar moieties. In certain embodiments, modified sugar moieties are bicyclic or tricyclic sugar moieties. In certain embodiments, modified sugar moieties are sugar surrogates. Such sugar surogates may comprise one or more substitutions corresponding to those of substituted sugar moieties.

In certain embodiments, modified sugar moieties are substituted sugar moieties comprising one or more substituent, including but not limited to substituents at the 2' and/or 5' positions. Examples of sugar substituents suitable for the 2'-position, include, but are not limited to: 2'-F, 2'-OCH$_3$ ("OMe" or "O-methyl"), and 2'-O(CH$_2$)$_2$OCH$_3$ ("MOE"). In certain embodiments, sugar substituents at the 2' position is selected from allyl, amino, azido, thio, O-allyl, O—C$_1$-C$_{10}$ alkyl, O—C$_1$-C$_{10}$ substituted alkyl; O—C$_1$-C$_{10}$ alkoxy; O—C$_1$-C$_{10}$ substituted alkoxy, OCF$_3$, O(CH$_2$)$_2$SCH$_3$, O(CH$_2$)$_2$—O—N(Rm)(Rn), and O—CH$_2$—C(=O)—N (Rm)(Rn), where each Rm and Rn is, independently, H or substituted or unsubstituted C$_1$-C$_{10}$ alkyl. Examples of sugar substituents at the 5'-position, include, but are not limited to: 5'-methyl (R or S); 5'-vinyl, and 5'-methoxy. In certain embodiments, substituted sugars comprise more than one non-bridging sugar substituent, for example, 2'-F-5'-methyl sugar moieties (see, e.g., PCT International Application WO 2008/101157, for additional 5', 2'-bis substituted sugar moieties and nucleosides).

Nucleosides comprising 2'-substituted sugar moieties are referred to as 2'-substituted nucleosides. In certain embodiments, a 2'-substituted nucleoside comprises a 2'-substituent group selected from halo, allyl, amino, azido, O—C$_1$-C$_{10}$ alkoxy; O—C$_1$-C$_{10}$ substituted alkoxy, SH, CN, OCN, CF$_3$, OCF$_3$, O-alkyl, S-alkyl, N(R$_m$)-alkyl; O-alkenyl, S-alkenyl, or N(R$_m$)-alkenyl; O-alkynyl, S-alkynyl, N(R$_m$)-alkynyl; O-alkylenyl-O-alkyl, alkynyl, alkaryl, aralkyl, O-alkaryl, O-aralkyl, O(CH$_2$)$_2$SCH$_3$, O—(CH$_2$)$_2$—O—N(R$_m$)(R$_n$) or O—CH$_2$—C(=O)—N(R$_m$)(R$_n$), where each R$_m$ and R$_n$ is, independently, H, an amino protecting group or substituted or unsubstituted C$_1$-C$_{10}$ alkyl. These 2'-substituent groups can be further substituted with one or more substituent groups independently selected from hydroxyl, amino, alkoxy, carboxy, benzyl, phenyl, nitro (NO$_2$), thiol, thioalkoxy (S-alkyl), halogen, alkyl, aryl, alkenyl and alkynyl.

In certain embodiments, a 2'-substituted nucleoside comprises a 2'-substituent group selected from F, NH$_2$, N$_3$, OCF$_3$, O—CH$_3$, O(CH$_2$)$_3$NH$_2$, CH$_2$—CH=CH$_2$, O—CH$_2$—CH=CH$_2$, OCH$_2$CH$_2$OCH$_3$, O(CH$_2$)$_2$SCH$_3$, O—(CH$_2$)$_2$—O—N(R$_m$)(R$_n$), O(CH$_2$)$_2$O(CH$_2$)$_2$N(CH$_3$)$_2$, and N-substituted acetamide (O—CH$_2$—C(=O)—N(R$_m$) (R$_n$)) where each R$_m$ and R$_n$ is, independently, H, an amino protecting group or substituted or unsubstituted C$_1$-C$_{10}$ alkyl.

In certain embodiments, a 2'-substituted nucleoside comprises a sugar moiety comprising a 2'-substituent group selected from F, OCF$_3$, O—CH$_3$, OCH$_2$CH$_2$OCH$_3$, O(CH$_2$)$_2$SCH$_3$, O—(CH$_2$)$_2$—O—N(CH$_3$)$_2$, —O(CH$_2$)$_2$O (CH$_2$)$_2$N(CH$_3$)$_2$, and O—CH$_2$—C(=O)—N(H)CH$_3$.

In certain embodiments, a 2'-substituted nucleoside comprises a sugar moiety comprising a 2'-substituent group selected from F, O—CH$_3$, and OCH$_2$CH$_2$OCH$_3$.

Certain modified sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. Examples of such 4' to 2' sugar substituents, include, but are not limited to: —[C(R$_a$)(R$_b$)]$_n$—, —[C(R$_a$)(R$_b$)]$_n$—O—, —C(R$_a$R$_b$)—N(R)—O— or, —C(R$_a$R$_b$)—O—N(R)—; 4'-CH$_2$-2', 4'-(CH$_2$)$_2$-2', 4'-(CH$_2$)$_3$-2', 4'-(CH$_2$)—O-2' (LNA); 4'-(CH$_2$)—S-2; 4'-(CH$_2$)$_2$—O-2' (ENA); 4'-CH(CH$_3$)—O-2' (cEt) and 4'-CH(CH$_2$OCH$_3$)—O-2', and analogs thereof (see, e.g., U.S. Pat. No. 7,399,845, issued on Jul. 15, 2008); 4'-C(CH$_3$)(CH$_3$)—O-2' and analogs thereof, (see, e.g., WO2009/006478, published Jan. 8, 2009); 4'-CH$_2$—N(OCH$_3$)-2' and analogs thereof (see, e.g., WO2008/150729, published Dec. 11, 2008); 4'-CH$_2$—O—N(CH$_3$)-2' (see, e.g., US2004/0171570, published Sep. 2, 2004); 4'-CH$_2$—O—N(R)-2', and 4'-CH$_2$—N(R)—O-2'-, wherein each R is, independently, H, a protecting group, or C$_1$-C$_{12}$ alkyl; 4'-CH$_2$—N(R)—O-2', wherein R is H, C$_1$-C$_{12}$ alkyl, or a protecting group (see, U.S. Pat. No. 7,427,672, issued on Sep. 23, 2008); 4'-CH$_2$—C(H)(CH$_3$)-2' (see, e.g., Chattopadhyaya, et al., *J. Org. Chem.,* 2009, 74, 118-134); and 4'-CH$_2$—C(=CH$_2$)-2' and analogs thereof (see, published PCT International Application WO 2008/154401, published on Dec. 8, 2008).

In certain embodiments, such 4' to 2' bridges independently comprise from 1 to 4 linked groups independently selected from —[C(R$_a$)(R$_b$)]$_n$—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_a$)—;

wherein:

x is 0, 1, or 2;

n is 1, 2, 3, or 4;

each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl, or a protecting group.

Nucleosides comprising bicyclic sugar moieties are referred to as bicyclic nucleosides or BNAs. Bicyclic nucleosides include, but are not limited to, (A) α-L-Methyleneoxy (4'-CH$_2$—O-2') BNA, (B) β-D-Methyleneoxy (4'-CH$_2$—O-2') BNA (also referred to as locked nucleic acid or LNA), (C) Ethyleneoxy (4'-(CH$_2$)$_2$—O-2') BNA, (D) Aminooxy (4'-CH$_2$—O—N(R)-2') BNA, (E) Oxyamino (4'-CH$_2$—N(R)—O-2') BNA, (F) Methyl(methyleneoxy) (4'-CH(CH$_3$)—O-2') BNA (also referred to as constrained ethyl or cEt), (G) methylene-thio (4'-CH$_2$—S-2') BNA, (H) methylene-amino (4'-CH2-N(R)-2') BNA, (I) methyl carbocyclic (4'-CH$_2$—CH(CH$_3$)-2') BNA, and (J) propylene carbocyclic (4'-(CH$_2$)$_3$-2') BNA as depicted below.

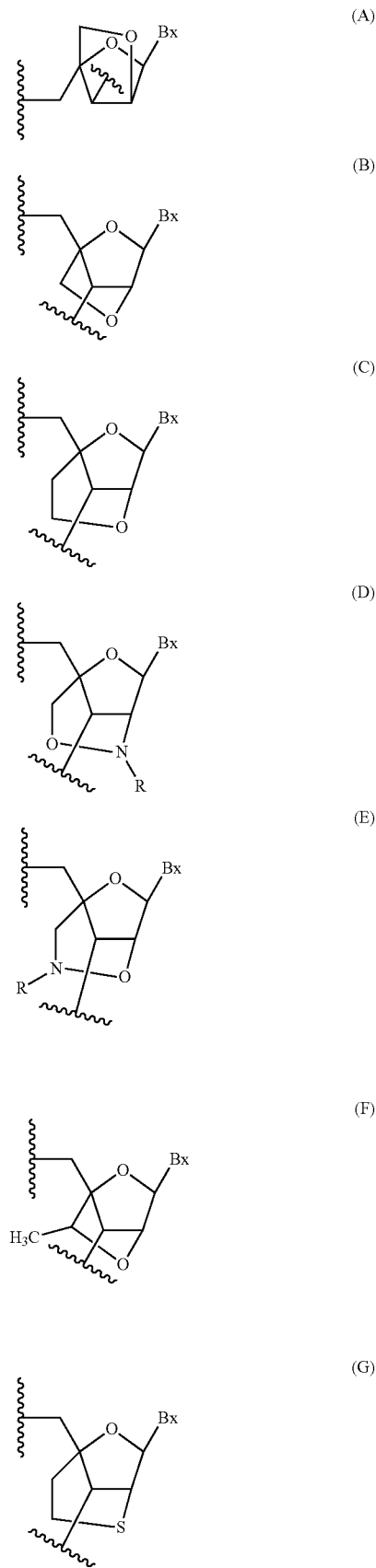

-continued

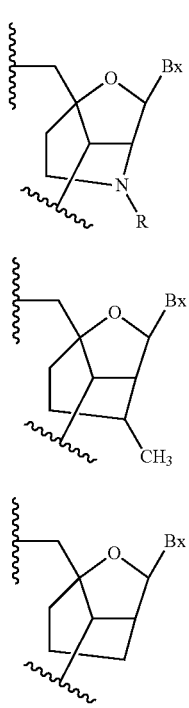

(H)

(I)

(J)

wherein Bx is a nucleobase moiety and R is, independently, H, a protecting group, or $C_1$-$C_{12}$ alkyl.

Additional bicyclic sugar moieties are known in the art, for example: Singh et al., *Chem. Commun.,* 1998, 4, 455-456; Koshkin et al., *Tetrahedron,* 1998, 54, 3607-3630; Wahlestedt et al., *Proc. Natl. Acad. Sci. U S. A.,* 2000, 97, 5633-5638; Kumar et al., *Bioorg. Med. Chem. Lett.,* 1998, 8, 2219-2222; Singh et al., *J. Org. Chem.,* 1998, 63, 10035-10039; Srivastava et al., *J. Am. Chem. Soc.,* 129(26) 8362-8379 (Jul. 4, 2007); Elayadi et al., *Curr. Opinion Invens. Drugs,* 2001, 2, 558-561; Braasch et al., *Chem. Biol.,* 2001, 8, 1-7; Orum et al., *Curr. Opinion Mol. Ther.,* 2001, 3, 239-243; U.S. Pat. Nos. 7,053,207, 6,268,490, 6,770,748, 6,794,499, 7,034,133, 6,525,191, 6,670,461, and 7,399,845; WO 2004/106356, WO 1994/14226, WO 2005/021570, and WO 2007/134181; U.S. Patent Publication Nos. US2004/0171570, US2007/0287831, and US2008/0039618; U.S. patent Ser. Nos. 12/129,154, 60/989,574, 61/026,995, 61/026,998, 61/056,564, 61/086,231, 61/097,787, and 61/099,844; and PCT International Applications Nos. PCT/US2008/064591, PCT/US2008/066154, and PCT/US2008/068922.

In certain embodiments, bicyclic sugar moieties and nucleosides incorporating such bicyclic sugar moieties are further defined by isomeric configuration. For example, a nucleoside comprising a 4'-2' methylene-oxy bridge, may be in the α-L configuration or in the β-D configuration. Previously, α-L-methyleneoxy (4'-$CH_2$—O-2') bicyclic nucleosides have been incorporated into antisense oligonucleotides that showed antisense activity (Frieden et al., *Nucleic Acids Research,* 2003, 21, 6365-6372).

In certain embodiments, substituted sugar moieties comprise one or more non-bridging sugar substituent and one or more bridging sugar substituent (e.g., 5'-substituted and 4'-2' bridged sugars). (see, PCT International Application WO 2007/134181, published on Nov. 22, 2007, wherein LNA is substituted with, for example, a 5'-methyl or a 5'-vinyl group).

In certain embodiments, modified sugar moieties are sugar surrogates. In certain such embodiments, the oxygen atom of the naturally occurring sugar is substituted, e.g., with a sulfur, carbon or nitrogen atom. In certain such embodiments, such modified sugar moiety also comprises bridging and/or non-bridging substituents as described above. For example, certain sugar surogates comprise a 4'-sulfur atom and a substitution at the 2'-position (see, e.g., published U.S. Patent Application US2005/0130923, published on Jun. 16, 2005) and/or the 5' position. By way of additional example, carbocyclic bicyclic nucleosides having a 4'-2' bridge have been described (see, e.g., Freier et al., *Nucleic Acids Research,* 1997, 25(22), 4429-4443 and Albaek et al., *J. Org. Chem.,* 2006, 71, 7731-7740).

In certain embodiments, sugar surrogates comprise rings having other than 5-atoms. For example, in certain embodiments, a sugar surrogate comprises a six-membered tetrahydropyran. Such tetrahydropyrans may be further modified or substituted. Nucleosides comprising such modified tetrahydropyrans include, but are not limited to, hexitol nucleic acid (HNA), anitol nucleic acid (ANA), manitol nucleic acid (MNA) (see Leumann, C J. *Bioorg. & Med. Chem.* (2002) 10:841-854), fluoro HNA (F-HNA), and those compounds having Formula VII:

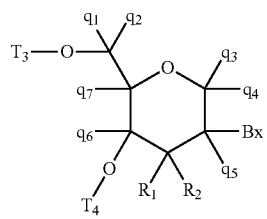

VII wherein independently for each of said at least one tetrahydropyran nucleoside analog of Formula VII:

Bx is a nucleobase moiety;

$T_3$ and $T_4$ are each, independently, an internucleoside linking group linking the tetrahydropyran nucleoside analog to the antisense compound or one of $T_3$ and $T_4$ is an internucleoside linking group linking the tetrahydropyran nucleoside analog to the antisense compound and the other of $T_3$ and $T_4$ is H, a hydroxyl protecting group, a linked conjugate group, or a 5' or 3'-terminal group; $q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or $NJ_1$, and each $J_1$, $J_2$, and $J_3$ is, independently, H or $C_1$-$C_6$ alkyl.

In certain embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VII are provided wherein one of $R_1$ and $R_2$ is F. In certain embodiments, $R_1$ is fluoro and $R_2$ is H, $R_1$ is methoxy and $R_2$ is H, and $R_1$ is methoxyethoxy and $R_2$ is H.

Many other bicyclic and tricyclic sugar and sugar surrogate ring systems are known in the art that can be used to modify nucleosides (see, e.g., review article: Leumann, J. C, *Bioorganic & Medicinal Chemistry*, 2002, 10, 841-854).

In certain embodiments, sugar surrogates comprise rings having more than 5 atoms and more than one heteroatom. For example nucleosides comprising morpholino sugar moieties and their use in oligomeric compounds has been reported (see for example: Braasch et al., Biochemistry, 2002, 41, 4503-4510; and U.S. Pat. Nos. 5,698,685; 5,166, 315; 5,185,444; and 5,034,506). As used here, the term "morpholino" means a sugar surrogate having the following structure:

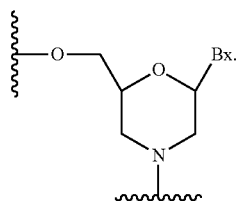

In certain embodiments, morpholinos may be modified, for example by adding or altering various substituent groups from the above morpholino structure. Such sugar surrogates are referred to herein as "modified morpholinos."

Combinations of modifications are also provided without limitation, such as 2'-F-5'-methyl substituted nucleosides (see PCT International Application WO 2008/101157 Published on Aug. 21, 2008 for other disclosed 5', 2'-bis substituted nucleosides) and replacement of the ribosyl ring oxygen atom with S and further substitution at the 2'-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'-$CH_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., *J. Am. Chem. Soc.* 2007, 129(26), 8362-8379).

Certain Nucleobases

In certain embodiments, nucleosides of the present invention comprise one or more unmodified nucleobases. In certain embodiments, nucleosides of the present invention comprise one or more modified nucleobases.

In certain embodiments, modified nucleobases are selected from: universal bases, hydrophobic bases, promiscuous bases, size-expanded bases, and fluorinated bases as defined herein. 5-substituted pyrimidines, 6-azapyrimidines and N-2, N-6 and O-6 substituted purines, including 2-aminopropyl-adenine, 5-propynyluracil; 5-propynylcytosine; 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein. Further modified nucleobases include tricyclic pyrimidines such as phenoxazine cytidine([5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, Kroschwitz, J. I., Ed., John Wiley & Sons, 1990, 858-859; those disclosed by Englisch et al., *Angewandte Chemie*, International Edition, 1991, 30, 613; and those disclosed by Sanghvi, Y. S., Chapter 15, *Antisense Research and Applications*, Crooke, S. T. and Lebleu, B., Eds., CRC Press, 1993, 273-288.

Representative United States patents that teach the preparation of certain of the above noted modified nucleobases as well as other modified nucleobases include without limitation, U.S. Pat. Nos. 3,687,808; 4,845,205; 5,130,302; 5,134, 066; 5,175,273; 5,367,066; 5,432,272; 5,457,187; 5,459, 255; 5,484,908; 5,502,177; 5,525,711; 5,552,540; 5,587, 469; 5,594,121; 5,596,091; 5,614,617; 5,645,985; 5,681, 941; 5,750,692; 5,763,588; 5,830,653 and 6,005,096, certain of which are commonly owned with the instant application, and each of which is herein incorporated by reference in its entirety.

Certain Internucleoside Linkages

In certain embodiments, the present invention provides oligomeric compounds comprising linked nucleosides. In such embodiments, nucleosides may be linked together using any internucleoside linkage. The two main classes of internucleoside linking groups are defined by the presence or absence of a phosphorus atom. Representative phosphorus containing internucleoside linkages include, but are not limited to, phosphodiesters (P═O), phosphotriesters, methylphosphonates, phosphoramidate, and phosphorothioates (P═S). Representative non-phosphorus containing internucleoside linking groups include, but are not limited to, methylenemethylimino (—$CH_2$—N($CH_3$)—O—$CH_2$—), thiodiester (—O—C(O)—S—), thionocarbamate (—O—C(O)(NH)—S—); siloxane (—O—Si(H)$_2$—O—); and N,N'-dimethylhydrazine (—$CH_2$—N($CH_3$)—N($CH_3$)—). Modified linkages, compared to natural phosphodiester linkages, can be used to alter, typically increase, nuclease resistance of the oligomeric compound. In certain embodiments, internucleoside linkages having a chiral atom can be prepared as a racemic mixture, or as separate enantiomers. Representative chiral linkages include, but are not limited to, alkylphosphonates and phosphorothioates. Methods of preparation of phosphorous-containing and non-phosphorous-containing internucleoside linkages are well known to those skilled in the art.

The oligonucleotides described herein contain one or more asymmetric centers and thus give rise to enantiomers, diastereomers, and other stereoisomeric configurations that may be defined, in terms of absolute stereochemistry, as (R) or (S), α or β such as for sugar anomers, or as (D) or (L) such as for amino acids etc. Included in the antisense compounds provided herein are all such possible isomers, as well as their racemic and optically pure forms.

Neutral internucleoside linkages include without limitation, phosphotriesters, methylphosphonates, MMI (3'-CH$_2$—N(CH$_3$)—O-5'), amide-3 (3'-CH$_2$—C(=O)—N(H)-5'), amide-4 (3'-CH$_2$—N(H)—C(=O)-5'), formacetal (3'-O—CH$_2$—O-5'), and thioformacetal (3'-S—CH$_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and CH$_2$ component parts.

Certain Motifs

In certain embodiments, the present invention provides oligomeric compounds comprising oligonucleotides. In certain embodiments, such oligonucleotides comprise one or more chemical modification. In certain embodiments, chemically modified oligonucleotides comprise one or more modified nucleosides. In certain embodiments, chemically modified oligonucleotides comprise one or more modified nucleosides comprising modified sugars. In certain embodiments, chemically modified oligonucleotides comprise one or more modified nucleosides comprising one or more modified nucleobases. In certain embodiments, chemically modified oligonucleotides comprise one or more modified internucleoside linkages. In certain embodiments, the chemically modifications (sugar modifications, nucleobase modifications, and/or linkage modifications) define a pattern or motif. In certain embodiments, the patterns of chemical modifications of sugar moieties, internucleoside linkages, and nucleobases are each independent of one another. Thus, an oligonucleotide may be described by its sugar modification motif, internucleoside linkage motif and/or nucleobase modification motif (as used herein, nucleobase modification motif describes the chemical modifications to the nucleobases independent of the sequence of nucleobases).

Certain Sugar Motifs

In certain embodiments, oligonucleotides comprise one or more type of modified sugar moieties and/or naturally occurring sugar moieties arranged along an oligonucleotide or region thereof in a defined pattern or sugar modification motif. Such motifs may include any of the sugar modifications discussed herein and/or other known sugar modifications.

In certain embodiments, the oligonucleotides comprise or consist of a region having a gapmer sugar modification motif, which comprises two external regions or "wings" and an internal region or "gap." The three regions of a gapmer motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap. In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar modification motifs of the two wings are the same as one another (symmetric gapmer). In certain embodiments, the sugar modification motifs of the 5'-wing differs from the sugar modification motif of the 3'-wing (asymmetric gapmer). In certain embodiments, oligonucleotides comprise 2'-MOE modified nucleosides in the wings and 2'-F modified nucleosides in the gap.

In certain embodiments, oligonucleotides are fully modified. In certain such embodiments, oligonucleotides are uniformly modified. In certain embodiments, oligonucleotides are uniform 2'-MOE. In certain embodiments, oligonucleotides are uniform 2'-F. In certain embodiments, oligonucleotides are uniform morpholino. In certain embodiments, oligonucleotides are uniform BNA. In certain embodiments, oligonucleotides are uniform LNA. In certain embodiments, oligonucleotides are uniform cEt.

In certain embodiments, oligonucleotides comprise a uniformly modified region and additional nucleosides that are unmodified or differently modified. In certain embodiments, the uniformly modified region is at least 5, 10, 15, or 20 nucleosides in length. In certain embodiments, the uniform region is a 2'-MOE region. In certain embodiments, the uniform region is a 2'-F region. In certain embodiments, the uniform region is a morpholino region. In certain embodiments, the uniform region is a BNA region. In certain embodiments, the uniform region is a LNA region. In certain embodiments, the uniform region is a cEt region.

In certain embodiments, the oligonucleotide does not comprise more than 4 contiguous unmodified 2'-deoxynucleosides. In certain circumstances, antisesense oligonucleotides comprising more than 4 contiguous 2'-deoxynucleosides activate RNase H, resulting in cleavage of the target RNA. In certain embodiments, such cleavage is avoided by not having more than 4 contiguous 2'-deoxynucleosides, for example, where alteration of splicing and not cleavage of a target RNA is desired.

Certain Internucleoside Linkage Motifs

In certain embodiments, oligonucleotides comprise modified internucleoside linkages arranged along the oligonucleotide or region thereof in a defined pattern or modified internucleoside linkage motif. In certain embodiments, internucleoside linkages are arranged in a gapped motif, as described above for sugar modification motif. In such embodiments, the internucleoside linkages in each of two wing regions are different from the internucleoside linkages in the gap region. In certain embodiments the internucleoside linkages in the wings are phosphodiester and the internucleoside linkages in the gap are phosphorothioate. The sugar modification motif is independently selected, so such oligonucleotides having a gapped internucleoside linkage motif may or may not have a gapped sugar modification motif and if it does have a gapped sugar motif, the wing and gap lengths may or may not be the same.

In certain embodiments, oligonucleotides comprise a region having an alternating internucleoside linkage motif. In certain embodiments, oligonucleotides of the present invention comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphorothioate. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide.

Certain Nucleobase Modification Motifs

In certain embodiments, oligonucleotides comprise chemical modifications to nucleobases arranged along the oligonucleotide or region thereof in a defined pattern or nucleobases modification motif. In certain such embodiments, nucleobase modifications are arranged in a gapped motif. In certain embodiments, nucleobase modifications are arranged in an alternating motif. In certain embodiments, each nucleobase is modified. In certain embodiments, none of the nucleobases is chemically modified.

In certain embodiments, oligonucleotides comprise a block of modified nucleobases. In certain such embodiments, the block is at the 3'-end of the oligonucleotide. In certain embodiments the block is within 3 nucleotides of the 3'-end of the oligonucleotide. In certain such embodiments, the block is at the 5'-end of the oligonucleotide. In certain embodiments the block is within 3 nucleotides of the 5'-end of the oligonucleotide.

In certain embodiments, nucleobase modifications are a function of the natural base at a particular position of an oligonucleotide. For example, in certain embodiments each purine or each pyrimidine in an oligonucleotide is modified. In certain embodiments, each adenine is modified. In certain embodiments, each guanine is modified. In certain embodiments, each thymine is modified. In certain embodiments, each cytosine is modified. In certain embodiments, each uracil is modified.

In certain embodiments, some, all, or none of the cytosine moieties in an oligonucleotide are 5-methyl cytosine moieties. Herein, 5-methyl cytosine is not a "modified nucleobase." Accordingly, unless otherwise indicated, unmodified nucleobases include both cytosine residues having a 5-methyl and those lacking a 5 methyl. In certain embodiments, the methylation state of all or some cytosine nucleobases is specified.

Certain Overall Lengths

In certain embodiments, the present invention provides oligomeric compounds including oligonucleotides of any of a variety of ranges of lengths. In certain embodiments, the invention provides oligomeric compounds or oligonucleotides consisting of X to Y linked nucleosides, where X represents the fewest number of nucleosides in the range and Y represents the largest number of nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X≤Y. For example, in certain embodiments, the invention provides oligomeric compounds which comprise oligonucleotides consisting of 8 to 9, 8 to 10, 8 to 11, 8 to 12, 8 to 13, 8 to 14, 8 to 15, 8 to 16, 8 to 17, 8 to 18, 8 to 19, 8 to 20, 8 to 21, 8 to 22, 8 to 23, 8 to 24, 8 to 25, 8 to 26, 8 to 27, 8 to 28, 8 to 29, 8 to 30, 9 to 10, 9 to 11, 9 to 12, 9 to 13, 9 to 14, 9 to 15, 9 to 16, 9 to 17, 9 to 18, 9 to 19, 9 to 20, 9 to 21, 9 to 22, 9 to 23, 9 to 24, 9 to 25, 9 to 26, 9 to 27, 9 to 28, 9 to 29, 9 to 30, 10 to 11, 10 to 12, 10 to 13, 10 to 14, 10 to 15, 10 to 16, 10 to 17, 10 to 18, 10 to 19, 10 to 20, 10 to 21, 10 to 22, 10 to 23, 10 to 24, 10 to 25, 10 to 26, 10 to 27, 10 to 28, 10 to 29, 10 to 30, 11 to 12, 11 to 13, 11 to 14, 11 to 15, 11 to 16, 11 to 17, 11 to 18, 11 to 19, 11 to 20, 11 to 21, 11 to 22, 11 to 23, 11 to 24, 11 to 25, 11 to 26, 11 to 27, 11 to 28, 11 to 29, 11 to 30, 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides. In embodiments where the number of nucleosides of an oligomeric compound or oligonucleotide is limited, whether to a range or to a specific number, the oligomeric compound or oligonucleotide may, nonetheless further comprise additional other substituents. For example, an oligonucleotide comprising 8-30 nucleosides excludes oligonucleotides having 31 nucleosides, but, unless otherwise indicated, such an oligonucleotide may further comprise, for example one or more conjugates, terminal groups, or other substituents. In certain embodiments, a gapmer oligonucleotide has any of the above lengths.

One of skill in the art will appreciate that certain lengths may not be possible for certain motifs. For example: a gapmer having a 5'-wing region consisting of four nucleotides, a gap consisting of at least six nucleotides, and a 3'-wing region consisting of three nucleotides cannot have an overall length less than 13 nucleotides. Thus, one would understand that the lower length limit is 13 and that the limit of 10 in "10-20" has no effect in that embodiment.

Further, where an oligonucleotide is described by an overall length range and by regions having specified lengths, and where the sum of specified lengths of the regions is less than the upper limit of the overall length range, the oligonucleotide may have additional nucleosides, beyond those of the specified regions, provided that the total number of nucleosides does not exceed the upper limit of the overall length range. For example, an oligonucleotide consisting of 20-25 linked nucleosides comprising a 5'-wing consisting of 5 linked nucleosides; a 3'-wing consisting of 5 linked nucleosides and a central gap consisting of 10 linked nucleosides (5+5+10=20) may have up to 5 nucleosides that are not part of the 5'-wing, the 3'-wing, or the gap (before reaching the overall length limitation of 25). Such additional nucleosides may be 5' of the 5'-wing and/or 3' of the 3' wing.

Certain Oligonucleotides

In certain embodiments, oligonucleotides of the present invention are characterized by their sugar motif, internucleoside linkage motif, nucleobase modification motif and overall length. In certain embodiments, such parameters are each independent of one another. Thus, each internucleoside linkage of an oligonucleotide having a gapmer sugar motif may be modified or unmodified and may or may not follow the gapmer modification pattern of the sugar modifications. Thus, the internucleoside linkages within the wing regions of a sugar-gapmer may be the same or different from one another and may be the same or different from the internucleoside linkages of the gap region. Likewise, such sugar-gapmer oligonucleotides may comprise one or more modified nucleobase independent of the gapmer pattern of the sugar modifications. Herein if a description of an oligonucleotide or oligomeric compound is silent with respect to one or more parameter, such parameter is not limited. Thus, an oligomeric compound described only as having a gapmer sugar motif without further description may have any length, internucleoside linkage motif, and nucleobase modification motif. Unless otherwise indicated, all chemical modifications are independent of nucleobase sequence.

Certain Conjugate Groups

In certain embodiments, oligomeric compounds are modified by attachment of one or more conjugate groups. In general, conjugate groups modify one or more properties of the attached oligomeric compound including but not limited to pharmacodynamics, pharmacokinetics, stability, binding, absorption, cellular distribution, cellular uptake, charge and clearance. Conjugate groups are routinely used in the chemical arts and are linked directly or via an optional conjugate linking moiety or conjugate linking group to a parent compound such as an oligomeric compound, such as an oligonucleotide. Conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes. Certain conjugate groups have been described previously, for example: cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., do-decan-diol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937).

In certain embodiments, a conjugate group comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indo-methicin, a barbiturate, a cephalosporin, a sulfa drug, an antidiabetic, an antibacterial or an antibiotic.

In certain embodiments, conjugate groups are directly attached to oligonucleotides in oligomeric compounds. In certain embodiments, conjugate groups are attached to oligonucleotides by a conjugate linking group. In certain such embodiments, conjugate linking groups, including, but not limited to, bifunctional linking moieties such as those known in the art are amenable to the compounds provided herein. Conjugate linking groups are useful for attachment of conjugate groups, such as chemical stabilizing groups, functional groups, reporter groups and other groups to selective sites in a parent compound such as for example an oligomeric compound. In general a bifunctional linking moiety comprises a hydrocarbyl moiety having two functional groups. One of the functional groups is selected to bind to a parent molecule or compound of interest and the other is selected to bind essentially any selected group such as chemical functional group or a conjugate group. In some embodiments, the conjugate linker comprises a chain structure or an oligomer of repeating units such as ethylene glycol or amino acid units. Examples of functional groups that are routinely used in a bifunctional linking moiety include, but are not limited to, electrophiles for reacting with nucleophilic groups and nucleophiles for reacting with electrophilic groups. In some embodiments, bifunctional linking moieties include amino, hydroxyl, carboxylic acid, thiol, unsaturations (e.g., double or triple bonds), and the like.

Some nonlimiting examples of conjugate linking moieties include pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other linking groups include, but are not limited to, substituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

Conjugate groups may be attached to either or both ends of an oligonucleotide (terminal conjugate groups) and/or at any internal position.

In certain embodiments, conjugate groups are at the 3'-end of an oligonucleotide of an oligomeric compound. In certain embodiments, conjugate groups are near the 3'-end. In certain embodiments, conjugates are attached at the 3'end of an oligomeric compound, but before one or more terminal group nucleosides. In certain embodiments, conjugate groups are placed within a terminal group. In certain embodiments, the present invention provides oligomeric compounds. In certain embodiments, oligomeric compounds comprise an oligonucleotide. In certain embodiments, an oligomeric compound comprises an oligonucleotide and one or more conjugate and/or terminal groups. Such conjugate and/or terminal groups may be added to oligonucleotides having any of the chemical motifs discussed above. Thus, for example, an oligomeric compound comprising an oligonucleotide having region of alternating nucleosides may comprise a terminal group.

Antisense Compounds

In certain embodiments, oligomeric compounds of the present invention are antisense compounds. Such antisense compounds are capable of hybridizing to a target nucleic acid, resulting in at least one antisense activity. In certain embodiments, antisense compounds specifically hybridize to one or more target nucleic acid. In certain embodiments, a specifically hybridizing antisense compound has a nucleobase sequence comprising a region having sufficient complementarity to a target nucleic acid to allow hybridization and result in antisense activity and insufficient complementarity to any non-target so as to avoid non-specific hybridization to any non-target nucleic acid sequences under conditions in which specific hybridization is desired (e.g., under physiological conditions for in vivo or therapeutic uses, and under conditions in which assays are performed in the case of in vitro assays).

In certain embodiments, the present invention provides antisense compounds comprising oligonucleotides that are fully complementary to the target nucleic acid over the entire length of the oligonucleotide. In certain embodiments, oligonucleotides are 99% complementary to the target nucleic acid. In certain embodiments, oligonucleotides are 95% complementary to the target nucleic acid. In certain embodiments, such oligonucleotides are 90% complementary to the target nucleic acid.

In certain embodiments, such oligonucleotides are 85% complementary to the target nucleic acid. In certain embodiments, such oligonucleotides are 80% complementary to the target nucleic acid. In certain embodiments, an antisense compound comprises a region that is fully complementary to a target nucleic acid and is at least 80% complementary to the target nucleic acid over the entire length of the oligonucleotide. In certain such embodiments, the region of full complementarity is from 6 to 14 nucleobases in length.

In certain embodiments antisense compounds and antisense oligonucleotides comprise single-strand compounds. In certain embodiments antisense compounds and antisense oligonucleotides comprise double-strand compounds.

Certain Target Nucleic Acids and Mechanisms

In certain embodiments, antisense compounds comprise or consist of an oligonucleotide comprising a region that is complementary to a target nucleic acid. In certain embodiments, the target nucleic acid is an endogenous RNA molecule. In certain embodiments, the target nucleic acid is a long non-coding RNA. In certain embodiments, the target nucleic acid is a SMN-NAT transcript. In certain embodiments, the target RNA has the sequence set forth in SEQ ID NO. 1.

In certain embodiments, natural antisense transcripts (NATs) are RNA transcripts encoded within a cell that have transcript complementarity to other RNA transcripts. In certain embodiments, natural antisense transcripts may play one or more roles in regulating expression of complementary RNA transcripts. For example, in certain embodiments, a natural antisense transcripts may serve to partially silence the expression of its complementary RNA transcript. Therefore, reducing the expression of certain natural antisense transcripts may increase expression of certain complementary RNA transcripts.

SMA is caused by the loss of both copies of survival motor neuron gene 1 (SMN1), which may also be known as SMN Telomeric, a protein that is part of a multi-protein complex thought to be involved in snRNP biogenesis and recycling. A nearly identical gene, SMN2, which may also be known as SMN Centromeric, exists in a duplicated region on chromosome 5q13 and modulates disease severity. Although SMN1 and SMN2 have the potential to code for the same protein, SMN2 contains a translationally silent mutation at position +6 of exon 7, which results in inefficient inclusion of exon 7 in SMN2 transcripts. In certain embodiments, a natural antisense transcript to SMN exists (e.g. SMN-NAT), and SMN-NAT is complementary to both SMN1 and SMN2. Therefore, in certain embodiments, SMN-NAT reduces expression of SMN1 and SMN2.

In instances where loss of SMN1 has occurred, SMN-NAT will reduce expression of SMN2, which may exacerbate symptoms associated with Spinal Muscular Atrophy. As discussed above, the severity of Spinal Muscular Atrophy correlates to the amount of function SMN protein produced by SMN2. Therefore, in certain embodiments, it is desirable to increase expression of SMN2. Although SMN2 contains a translationally silent mutation at position +6 of exon 7, which results in inefficient inclusion of exon 7 in SMN2 transcripts, the SMN2 gene will produce copies of functional SMN (e.g. SMN mRNA containing exon 7, which are then translated into full-length SMN protein). In certain embodiments, increased expression of SMN2 results in increased amounts of functional SMN protein containing amino acids encoded by exon 7. In certain embodiments, reduction of SMN-NAT increases expression of SMN2 and increases the amount of functional SMN protein.

Certain embodiments disclosed herein are drawn to a method of inducing expression of SMN in a cell comprising contacting the cell with an antisense compound targeted to SMN-NAT. In several aspects, SMN-NAT comprises a nucleic acid sequence at least 85% identical to SEQ ID NO:1.

Certain Pharmaceutical Compositions

In certain embodiments, the present invention provides pharmaceutical compositions comprising one or more antisense compound. In certain embodiments, such pharmaceutical composition comprises a suitable pharmaceutically acceptable diluent or carrier. In certain embodiments, a pharmaceutical composition comprises a sterile saline solution and one or more antisense compound. In certain embodiments, such pharmaceutical composition consists of a sterile saline solution and one or more antisense compound. In certain embodiments, the sterile saline is pharmaceutical grade saline. In certain embodiments, a pharmaceutical composition comprises one or more antisense compound and sterile water. In certain embodiments, a pharmaceutical composition consists of one or more antisense compound and sterile water. In certain embodiments, the sterile saline is pharmaceutical grade water. In certain embodiments, a pharmaceutical composition comprises one or more antisense compound and phosphate-buffered saline (PBS). In certain embodiments, a pharmaceutical composition consists of one or more antisense compound and sterile phosphate-buffered saline (PBS). In certain embodiments, the sterile saline is pharmaceutical grade PBS.

In certain embodiments, antisense compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

Pharmaceutical compositions comprising antisense compounds encompass any pharmaceutically acceptable salts, esters, or salts of such esters. In certain embodiments, pharmaceutical compositions comprising antisense compounds comprise one or more oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an oligomeric compound which are cleaved by endogenous nucleases within the body, to form the active antisense oligomeric compound.

Lipid moieties have been used in nucleic acid therapies in a variety of methods. In certain such methods, the nucleic acid is introduced into preformed liposomes or lipoplexes made of mixtures of cationic lipids and neutral lipids. In certain methods, DNA complexes with mono- or poly-cationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions provided herein comprise one or more modified oligonucleotides and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, a pharmaceutical composition provided herein comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition provided herein comprises one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, a pharmaceutical composition provided herein comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition provided herein is prepared for oral administration. In certain embodiments, pharmaceutical compositions are prepared for buccal administration.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

In certain embodiments, a pharmaceutical composition is prepared for transmucosal administration. In certain of such embodiments penetrants appropriate to the barrier to be permeated are used in the formulation. Such penetrants are generally known in the art.

In certain embodiments, a pharmaceutical composition provided herein comprises an oligonucleotide in a therapeutically effective amount. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, one or more modified oligonucleotide provided herein is formulated as a prodrug. In certain embodiments, upon in vivo administration, a prodrug is chemically converted to the biologically, pharmaceutically or therapeutically more active form of an oligonucleotide. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, prodrugs are less water soluble than the corresponding active form. In certain instances, such prodrugs possess superior transmittal across cell membranes, where water solubility is detrimental to mobility. In certain embodiments, a prodrug is an ester. In certain such embodiments, the ester is metabolically hydrolyzed to carboxylic acid upon administration. In certain instances the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form.

In certain embodiments, the present invention provides compositions and methods for reducing the amount or activity of a target nucleic acid in a cell. In certain embodiments, the cell is in an animal. In certain embodiments, the animal is a mammal. In certain embodiments, the animal is a rodent. In certain embodiments, the animal is a primate. In certain embodiments, the animal is a non-human primate. In certain embodiments, the animal is a human.

In certain embodiments, the present invention provides methods of administering a pharmaceutical composition comprising an oligomeric compound of the present invention to an animal. Suitable administration routes include, but are not limited to, oral, rectal, transmucosal, intestinal, enteral, topical, suppository, through inhalation, intrathecal, intracerebroventricular, intraperitoneal, intranasal, intraocular, intratumoral, and parenteral (e.g., intravenous, intramuscular, intramedullary, and subcutaneous). In certain embodiments, pharmaceutical intrathecals are administered to achieve local rather than systemic exposures. For example, pharmaceutical compositions may be injected directly in the area of desired effect (e.g., into the eyes, ears).

Nonlimiting Disclosure and Incorporation by Reference

While certain compounds, compositions and methods described herein have been described with specificity in accordance with certain embodiments, the following examples serve only to illustrate the compounds described herein and are not intended to limit the same. Each of the references, GenBank accession numbers, and the like recited herein is hereby incorporated by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine (methylated uracil) for natural uracil of RNA).

Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other unmodified bases, such as "AT$^{me}$CGAUCG," wherein $^{me}$C indicates a cytosine base comprising a methyl group at the 5-position.

EXAMPLES

The following examples illustrate certain embodiments of the present disclosure and are not limiting. Moreover, where specific embodiments are provided, the inventors have contemplated generic application of those specific embodiments. For example, disclosure of an oligonucleotide having a particular motif provides reasonable support for additional oligonucleotides having the same or similar motif. And, for example, where a particular high-affinity modification appears at a particular position, other high-affinity modifications at the same position are considered suitable, unless otherwise indicated.

Example 1: Effect of Antisense Oligonucleotides Targeting SMN-NAT

Antisense oligonucleotides were designed targeting the SMN-NAT sequence, described herein as SEQ ID NO: 1 (GenBank accession # BC045789.1) and were tested for their effects on reducing the expression of SMN-NAT in HEK293T cells. As shown in Table 1, antisense oligonucleotides are effective at reducing expression of SMN-NAT.

The newly designed antisense oligonucleotides in Table 1 were designed as 5-10-5 MOE gapmers. The gapmers are 20 nucleosides in length, wherein the central gap segment comprises of ten 2'-deoxynucleosides and is flanked by wing segments on the 5' direction and the 3' direction comprising five nucleosides each. Each nucleoside in the 5' wing segment and each nucleoside in the 3' wing segment has a 2'-MOE modification. The internucleoside linkages throughout each gapmer are phosphorothioate (P=S) linkages. All cytosine residues throughout each gapmer are 5-methylcytosines.

TABLE 1

Antisense oligonucleotides targeted to SMN-NAT

| IsisNo | Sequence | % Reduction of SMN-NAT | Start Site Seq ID: 1 | Stop Site Seq ID: 1 | SEQ ID NO. |
|---|---|---|---|---|---|
| 658741 | GTACTACACTTTTAATTACT | 0.00 | 1 | 20 | 2 |
| 658742 | TGTATATTGATGTCAGTACT | 9.81 | 16 | 35 | 3 |
| 658743 | TACATTGTCTATTAGTGTAT | 0.00 | 31 | 50 | 4 |
| 658744 | TGACTCTCAATTCTGTTACA | 0.00 | 47 | 66 | 5 |
| 658745 | TCACAGGGCTATTTCTGACT | 0.00 | 62 | 81 | 6 |
| 658746 | AATCAGTCACATATATCACA | 70.85 | 77 | 96 | 7 |

TABLE 1-continued

Antisense oligonucleotides targeted to SMN-NAT

| IsisNo | Sequence | % Reduction of SMN-NAT | Start Site Seq ID: 1 | Stop Site Seq ID: 1 | SEQ ID NO. |
|---|---|---|---|---|---|
| 658747 | TGTAACTTTAGTTAAAATCA | 60.93 | 92 | 111 | 8 |
| 658748 | CTATTAAACCACATTTGTAA | 32.31 | 107 | 126 | 9 |
| 658749 | ACTACTATGCTTTCTCTATT | 0.00 | 122 | 141 | 10 |
| 658750 | CCACCATTTCTTGAAACTAC | 0.00 | 137 | 156 | 11 |
| 658751 | TTTCCAATAGTTTTACCACC | 0.00 | 152 | 171 | 12 |
| 658752 | GTTTTTGCATAAGGATTTCC | 26.89 | 167 | 186 | 13 |
| 658753 | GTGGAAATTTGGTTTGTTTT | 0.00 | 182 | 201 | 14 |
| 658754 | TGTGGCTCAGTGTAGGTGGA | 0.00 | 197 | 216 | 15 |
| 658755 | GTATTAATTCTTATATGTGG | 0.00 | 212 | 231 | 16 |
| 658756 | TTAGTTTTACACTTAGGTCT | 11.16 | 244 | 263 | 17 |
| 658757 | ACACAGTTTAGAGTTTTAGT | 0.00 | 259 | 278 | 18 |
| 658758 | GATCACAGATTTTTCTCTCT | 38.43 | 290 | 309 | 19 |
| 658759 | TTATAGGCAATCCATGATCA | 20.70 | 305 | 324 | 20 |
| 658760 | CATTTCAGTTTGTTCTTTTG | 53.97 | 325 | 344 | 21 |
| 658761 | CCCAGGCAACAAGGCCATTT | 16.58 | 340 | 359 | 22 |
| 658762 | GAACCTCGGGTGCCACCCCA | 0.00 | 356 | 375 | 23 |
| 658763 | CGTCCTTGATTTCCTCAGCG | 25.83 | 385 | 404 | 24 |
| 658764 | ACACCCTTGGTGTGTCAGCG | 35.68 | 403 | 422 | 25 |
| 658765 | TTCTGCTCTAGCCTCACACC | 0.00 | 418 | 437 | 26 |
| 658766 | GGAGAGAGCTAGTCTCTTTC | 0.00 | 453 | 472 | 27 |
| 658767 | AGGACCTCTCTCTGCAGGAG | 74.78 | 469 | 488 | 28 |
| 658768 | ATGGGAACTCTTTTCAGGAC | 0.00 | 484 | 503 | 29 |
| 658769 | GCATTTCACTGTGGAATGGG | 0.00 | 499 | 518 | 30 |
| 658770 | TTTATAAAAATGCTTGCATT | 81.60 | 514 | 533 | 31 |
| 658771 | CTTCCCATTAGCTCATTTAT | 68.30 | 529 | 548 | 32 |
| 658772 | TAGATAAGCTACCCCCTTCC | 0.00 | 544 | 563 | 33 |
| 658773 | TTTGCTCCCTATGTGTAGAT | 34.09 | 559 | 578 | 34 |
| 658774 | GGTCCTAACTGGTTTTTTGC | 55.30 | 574 | 593 | 35 |
| 658775 | CAGATGGCAACACCTGGTCC | 0.00 | 589 | 608 | 36 |
| 658776 | GATTCACGCTCTGTGCAGAT | 0.00 | 604 | 623 | 37 |
| 658777 | GCCTGCATAATAAAAGGTTG | 0.00 | 641 | 660 | 38 |
| 658778 | TCAGGCCAAGGACCTGCCTG | 73.05 | 656 | 675 | 39 |
| 658779 | TAAGCAATGTGGAGTAGCTC | 45.19 | 674 | 693 | 40 |
| 658780 | ACAATAGGAAAGAGATAAGC | 46.19 | 689 | 708 | 41 |
| 658781 | TTATTTAGCACATGCACAAT | 0.00 | 704 | 723 | 42 |
| 658782 | TGGCTCCACCTCCCCTTATT | 4.82 | 719 | 738 | 43 |
| 658783 | GCATGTCCACCATGGTGGCT | 92.56 | 734 | 753 | 44 |

TABLE 1-continued

Antisense oligonucleotides targeted to SMN-NAT

| IsisNo | Sequence | % Reduction of SMN-NAT | Start Site Seq ID: 1 | Stop Site Seq ID: 1 | SEQ ID NO. |
|---|---|---|---|---|---|
| 658784 | AGCTGCACGGAGAGAAAGGG | 47.38 | 768 | 787 | 45 |
| 658785 | GCATGTTGTGAGTTGTTGGG | 0.00 | 797 | 816 | 46 |
| 658786 | TCAGATAAGGAAGCTGGAAG | 0.00 | 820 | 839 | 47 |
| 658787 | GACCTTAGTACATACTCAGA | 0.00 | 835 | 854 | 48 |
| 658788 | GAAGTAAACACAGTGGACCT | 0.00 | 850 | 869 | 49 |
| 658789 | GTATGTGAAGTAAACACAGT | 0.00 | 856 874 | 875 893 | 50 |
| 658790 | GTAAACACAGTATGTGAAGT | 56.26 | 865 | 884 | 51 |
| 658791 | AGGTGGGTATGTGAAGTAAA | 0.00 | 880 | 899 | 52 |
| 658792 | ATCAGCAAGCTTCACATACG | 20.31 | 902 | 921 | 53 |
| 658793 | GGAGCTTCCTGGGTAATCAG | 0.00 | 917 | 936 | 54 |
| 658794 | AGCAGCTCTGGCACAGAGGG | 0.00 | 937 | 956 | 55 |
| 658795 | AAACATGTATAAGGAAGCAG | 52.59 | 952 | 971 | 56 |
| 658796 | GGAAGATCGGGCTGTAAACA | 54.20 | 967 | 986 | 57 |
| 658797 | ACTTCTCTTCTAACAAGGAG | 73.05 | 993 | 1012 | 58 |
| 658798 | CAGAGTCCTCGGTAGAACTT | 91.02 | 1043 | 1062 | 59 |
| 658799 | AAGCCGATAGTTAGACAGAG | 0.00 | 1058 | 1077 | 60 |
| 658800 | AAAAAAGACTAGGTAAGCC | 0.00 | 1073 | 1092 | 61 |
| 658801 | GTTTTGAGAGAGGAGGTAAA | 15.76 | 1090 | 1109 | 62 |
| 658802 | GTTTTTTCTTTGATGGTTTT | 66.43 | 1105 | 1124 | 63 |
| 658803 | GAAATCTAATTTTTCAGTTT | 93.98 | 1121 | 1140 | 64 |
| 658804 | AATCTTAATTTTGCTGAAAT | 37.35 | 1136 | 1155 | 65 |
| 658805 | TTTTTAAGAACAGAAAATCT | 57.27 | 1151 | 1170 | 66 |
| 658806 | ACACTTTGGTTTTTCATTTT | 60.18 | 1183 | 1202 | 67 |
| 658807 | ATTTTCTCCCGGTTTACACT | 60.00 | 1198 | 1217 | 68 |
| 658808 | AGGTAACTTGCATGTATTTT | 0.00 | 1213 | 1232 | 69 |
| 658809 | AATATCTTTATCAGATAGGT | 0.00 | 1229 | 1248 | 70 |
| 658810 | ATGTTTGCTGGGTACAATAT | 51.71 | 1244 | 1263 | 71 |
| 658811 | GTTTGAGAGTTCTTCATGTT | 0.00 | 1259 | 1278 | 72 |
| 658812 | CATCTTTTAATTGAATTTTT | 0.00 | 1290 | 1309 | 73 |
| 658813 | CCCGGCCAACTTACCCATCT | 0.00 | 1305 | 1324 | 74 |
| 658814 | GATTGGGATTGCAAGTATGA | 0.00 | 1334 | 1353 | 75 |
| 658815 | GAGCACACGCCACAATGCCT | 0.90 | 1456 | 1475 | 76 |
| 658816 | AGTCTTCTTGTCTCAGCCTT | 0.00 | 1494 | 1513 | 77 |
| 658817 | CCACCTCCTGCGCTCAGTCT | 0.00 | 1509 | 1528 | 78 |
| 658818 | TCACACAGCCTACTGCAGCC | 0.00 | 1530 | 1549 | 79 |

Example 2: Effect of Antisense Oligonucleotides Targeting SMN-NAT on SMN RNA Two antisense oligonucleotides from Example 1 above, Isis Nos. 658803 and 658798 were chosen for further evaluation for effects on increasing SMN transcription in HEK293T cells. A scrambled ASO not complementary to SMN-NAT was used as a control. HEK293T cells were transfected with Lipofectamine-2000 (Life Technologies) according to manufacturer's instructions and RNA was collected 24 hours after transfection. Standard RT-qPCR was used to assess SMN-NAT, SMN pre-mRNA and FL-SMN (full-length SMN) mRNA levels. As shown in Table 2, antisense oligonucleotides designed to reduce expression of SMN-NAT can effectively increase expression of SMN pre-mRNA and full length SMN mRNA in a dose dependent manner.

TABLE 2

Effect of antisense oligonucleotides targeting SMN-NAT

| Isis No. | Dose | Relative Levels | | |
| --- | --- | --- | --- | --- |
| | | SMN-NAT | SMN pre-mRNA | FL-SMN mRNA |
| 141923 | 0 nM | 1.13 | 0.85 | 0.95 |
| | 62.5 nM | 1.10 | 1.00 | 1.12 |
| | 12 5 nM | 1.15 | 0.86 | 1.23 |
| | 250 nM | 0.99 | 1.05 | 0.97 |
| | 500 nM | 1.13 | 1.03 | 1.13 |
| 658803 | 0 nM | 0.99 | 1.12 | 1.00 |
| | 62.5 nM | 0.58 | 1.05 | 1.16 |
| | 125 nM | 0.48 | 1.36 | 1.39 |
| | 250 nM | 0.31 | 1.68 | 1.83 |
| | 500 nM | 0.16 | 1.63 | 1.65 |
| 658798 | 0 nM | 1.03 | 0.95 | 1.03 |
| | 62.5 nM | 0.84 | 1.10 | 1.03 |
| | 125 nM | 0.69 | 1.30 | 1.29 |
| | 250 nM | 0.52 | 1.61 | 1.49 |
| | 500 nM | 0.31 | 1.58 | 1.74 |

Example 3: Effect of Antisense Oligonucleotides Targeting SMN-NAT on SMN RNA in SMA Fibroblasts Antisense oligonucleotide Isis No 658803 was used in a SMA fibroblast line (GM03813, Coriell) and in a carrier fibroblast line (GM03814, Coriell). Fibroblasts were transfected with Cytofectin with various concentrations (0 nM to 100 nM) of antisense oligonucleotide. Forty-eight hours after transfection, protein lysates were collected and SMN protein levels were determined by Western blot analysis. Histone H3 was used as a loading control. Signal intensity was determined using ImageJ gel analysis tool (NIH) and SMN levels were normalized to H3 levels. As shown in Table 3, antisense oligonucleotides designed to reduce expression of SMN-NAT increased expression of SMN protein in a dose dependent manner.

TABLE 3

Antisense oligonucleotides targeting SMN-NAT in SMA Fibroblasts

| Isis No. | Dose (nM) | Relative SMN protein Levels (AU) | |
| --- | --- | --- | --- |
| | | GM03813 SMA | GM03814 Carrier |
| Isis No. 658803 | 0 | 1.00 | 1.86 |
| | 6 | 1.19 | 2.09 |

TABLE 3-continued

Antisense oligonucleotides targeting SMN-NAT in SMA Fibroblasts

| Isis No. | Dose (nM) | Relative SMN protein Levels (AU) | |
| --- | --- | --- | --- |
| | | GM03813 SMA | GM03814 Carrier |
| | 12 | 1.19 | 2.16 |
| | 25 | 1.85 | 1.98 |
| | 50 | 1.98 | 2.12 |
| | 100 | 1.18 | 2.15 |

Example 4: Effect of Antisense Oligonucleotides Targeting SMN-NAT on SMN RNA in Primary SMA Neurons Antisense oligonucleotide Isis No 658803 was used to evaluate levels of SMN pre-mRNA and FL-SMN mRNA in primary cortical neurons isolated from E13.5 embryos of SMA mice (the SMN Δ7 mouse model, Stock number 005025, The Jackson laboratory). Five μM antisense oligonucleotide was added to the growth medium 2 days after plating out and incubated for 4 days. SMN-NAT, SMN pre-mRNA and FL-SMN mRNA levels were measured using RT-qPCR. As shown in Table 4 below, antisense oligonucleotides designed to reduce expression of SMN-NAT increased expression of SMN pre-mRNA and full length SMN mRNA in primary SMA neurons.

TABLE 4

Effect of antisense oligonucleotides targeting SMN-NAT on SMN RNA in Primary SMA neurons

| Isis No. | Relative Levels | | |
| --- | --- | --- | --- |
| | SMN-NAT | SMN pre-MRNA | FL-SMN mRNA |
| Untreated | 0.98 | 1.06 | 1.13 |
| 141923 (scrambled) | 1.01 | 1.13 | 1.11 |
| 658803 | 0.35 | 1.94 | 1.79 |

Example 5: Dose Response of Antisense Oligonucleotides Targeting SMN-NAT in HeLa Cells SMN-NAT targeting antisense oligonucleotides selected from Table 1 were tested for dose response analysis in HeLa cells. Oligonucleotide Scrb1, which does not target SMN-NAT, and Isis Number 387954, which targets SMN pre-mRNA, were used as negative controls. Cells were electroporated with 0, 6, 12, 25, 50, or 100 nM of antisense oligonucleotide, and SMN-NAT mRNA was analyzed as described in Example 2. Results are presented in Table 5 below. The results show that the antisense oligonucleotides targeting SMN-NAT inhibited SMN-NAT mRNA expression in a dose dependent manner.

TABLE 5

Effect of antisense oligonuclotides targeting SMN-NAT on SMN RNA in HeLa Cells

| Isis No. | Dose (nM) | SMN-NAT Relative levels |
|---|---|---|
| 658761 | 0 | 0.99 |
|  | 6 | 0.89 |
|  | 12 | 0.67 |
|  | 25 | 0.45 |
|  | 50 | 0.37 |
|  | 100 | 0.22 |
| 658764 | 0 | 1.09 |
|  | 6 | 0.67 |
|  | 12 | 0.54 |
|  | 25 | 0.44 |
|  | 50 | 0.43 |
|  | 100 | 0.32 |
| 658765 | 0 | 1.09 |
|  | 6 | 0.88 |
|  | 12 | 0.79 |
|  | 25 | 0.63 |
|  | 50 | 0.51 |
|  | 100 | 0.44 |
| 658792 | 0 | 2.02 |
|  | 6 | 1.06 |
|  | 12 | 0.83 |
|  | 25 | 0.52 |
|  | 50 | 0.36 |
|  | 100 | 0.25 |
| 658798 | 0 | 1.05 |
|  | 6 | 0.83 |
|  | 12 | 0.74 |
|  | 25 | 0.52 |
|  | 50 | 0.35 |
|  | 100 | 0.22 |
| 658802 | 0 | 1.02 |
|  | 6 | 0.95 |
|  | 12 | 0.66 |
|  | 25 | 0.49 |
|  | 50 | 0.41 |
|  | 100 | 0.17 |
| 658803 | 0 | 0.98 |
|  | 6 | 0.86 |
|  | 12 | 0.70 |
|  | 25 | 0.47 |
|  | 50 | 0.41 |
|  | 100 | 0.25 |
| 658815 | 0 | 1.05 |
|  | 6 | 0.83 |
|  | 12 | 0.55 |
|  | 25 | 0.45 |
|  | 50 | 0.36 |
|  | 100 | 0.32 |
| Scrb1 | 0 | 0.94 |
|  | 6 | 1.09 |
|  | 12 | 0.89 |
|  | 25 | 1.00 |
|  | 50 | 1.12 |
|  | 100 | 1.07 |
| 387954 | 0 | 1.12 |
|  | 6 | 1.23 |
|  | 12 | 1.30 |
|  | 25 | 1.19 |
|  | 50 | 1.21 |
|  | 100 | 1.07 |

Example 6: Effect of Antisense Oligonucleotides on SMN-NAT in SMA Mice

Antisense oligonucleotides targeting the SMN-NAT sequence, described herein as SEQ ID NO: 1 (GenBank accession # BC045789.1) were tested for their effects on SMN-NAT expression in adult SMA mice.

The antisense oligonucleotides in Table 6 were designed as 5-10-5 MOE gapmers having a mixed backbone (MBB). The gapmers are 20 nucleosides in length, wherein the central gap segment comprises ten 2'-deoxynucleosides and is flanked by wing segments on the 5' direction and the 3' direction comprising five nucleosides each. Each nucleoside in the 5' wing segment and each nucleoside in the 3' wing segment has a 2'-MOE modification. The internucleoside linkages throughout each gapmer are each independently selected from phosphorothioate (P=S) linkages and phosphodiester linkages. A subscript "o" denotes the location of the phosphodiester internucleoside linkages, all other internucleoside linkages are P=S linkages. All cytosine residues throughout each gapmer are 5-methylcytosines.

TABLE 6

Antisense oligonucleotides targeted to SMN-NAT

| Isis No | Sequence | Start Site Seq ID: 1 | Stop Site Seq ID: 1 | SEQ ID NO. |
|---|---|---|---|---|
| 813208 | CA$_o$G$_o$A$_o$G$_o$TCCT CGGTAGA$_o$A$_o$CTT | 1043 | 1062 | 59 |
| 813209 | GA$_o$A$_o$A$_o$T$_o$CTAA TTTTTCA$_o$G$_o$TTT | 1121 | 1140 | 64 |

Adult SMA mice (Jax #005058) received an intracerebroventricular (ICV) injection of 500 μg antisense oligonucleotide in PBS or an injection of PBS only. After 15 days, the mice were euthanized and total RNA and protein were isolated from the brain and spinal cord. SMN-NAT RNA levels and FL-SMN2 RNA levels were measured by RT-qPCR as described in example 2. The SMN/GAPDH protein ratio was measured by western blot analysis using antibodies against SMN and GAPDH. Signal intensity was measured with ImageJ gel analysis tool, and SMN values were normalized to GAPDH values. Isis No. 449323, which targets SMN pre-mRNA and corrects splicing was included as a positive control.

TABLE 7

Effect of antisense oligonucleotides on SMN-NAT expression in adult SMA mice

| | Relative Levels in the Brain | | | Relative Levels in the Spinal Cord | | |
|---|---|---|---|---|---|---|
| Isis No. | SMN-NAT | FL-SMN2 mRNA | SMN/GADPH | SMN-NAT | FL-SMN2 mRNA | SMN/GADPH |
| PBS | 0.97 | 1.03 | 0.91 | 1.02 | 1.08 | 0.21 |
| 449323 | 1.05 | 3.08 | 1.38 | 1.04 | 3.18 | 0.58 |
| 813208 | 0.41 | 1.05 | 0.65 | 0.65 | 0.97 | 0.18 |
| 813209 | 0.30 | 0.93 | 0.64 | 0.36 | 0.95 | 0.21 |

Example 7: Effect of Systemic Administration of Antisense Oligonucleotides on Neonatal SMA Mice Groups of 3 SMA mice (Jax #005025) received a single subcutaneous dose of 300 ug/g of an antisense oligonucleotide (ASO) listed in the table below on post-natal day 1 and a second dose of 300 ug/g ASO on post-natal day 3. Each group of mice received either a scrambled control ASO (Isis No. 141923), an ASO designed to knock down SMN-NAT (Isis No. 813208), or an SMN2 splicing ASO (Isis No. 449323). A group of 3 wild-type mice that did not receive any treatment was also used as a control (WT). After 10 days, the mice were sacrificed and relative levels of SMN-NAT, FL-SMN2 mRNA, and SMN protein relative to GAPDH were measured by RT-qPCR in both the brain and spinal cord.

TABLE 8

Effect of systemic administration of antisense oligonucleotides on SMN-NAT expression in SMA mice

| Isis No. | Mouse genotype | Relative Levels in the Brain | | | Relative Levels in the Spinal Cord | | |
|---|---|---|---|---|---|---|---|
| | | SMN-NAT | FL-SMN2 mRNA | SMN/GADPH | SMN-NAT | FL-SMN2 mRNA | SMN/GAPDH |
| N/A | WT | 1.09 | 1.06 | 2.38 | 0.81 | 1.15 | 1.68 |
| 141923 | SMA | 1.11 | 1.07 | 0.93 | 1.00 | 1.32 | 0.65 |
| 449323 | SMA | 1.09 | 1.59 | 1.90 | 0.83 | 1.79 | 1.51 |
| 813208 | SMA | 0.72 | 1.32 | 1.34 | 0.58 | 1.99 | 0.95 |

What is claimed:

1. A method of increasing SMN expression in a cell, comprising contacting the cell with an antisense compound, wherein the antisense compound comprises an oligonucleotide consisting of 12 to 30 linked nucleosides, wherein the oligonucleotide is at least 85% complementary to a SMN-NAT nucleic acid sequence, wherein the SMN-NAT nucleic acid sequence is at least 85% identical to SEQ ID NO: 1.

2. The method of claim 1, wherein the SMN-NAT nucleic acid sequence is at least 90% identical to SEQ ID NO: 1.

3. The method of claim 1, wherein the SMN-NAT nucleic acid sequence is 100% identical to SEQ ID NO: 1.

4. The method of claim 1, wherein the oligonucleotide is at least 90% complementary over its entire length to an equal length region of a SMN-NAT nucleic acid sequence.

5. The method of claim 1, wherein the oligonucleotide is at least 95% complementary over its entire length to an equal length region of a SMN-NAT nucleic acid sequence.

6. The method of claim 1, wherein the oligonucleotide is 100% complementary over its entire length to an equal length region of a SMN-NAT nucleic acid sequence.

7. The method of claim 1, wherein the oligonucleotide is a single-stranded oligonucleotide.

8. The method of claim 1, wherein the oligonucleotide is a modified oligonucleotide.

9. The method of claim 8, wherein the modified oligonucleotide consists of 12 to 30 linked nucleosides and has a nucleobase sequence comprising at least 8 contiguous nucleobases of any of the nucleobase sequences of SEQ ID NOs: 3, 7, 8, 9, 13, 17, 19, 20, 21, 22, 24, 25, 28, 31, 32, 34, 35, 39, 40, 41, 43, 44, 45, 51, 53, 56, 57, 58, 59, 62, 63, 64, 65, 66, 67, 68, 71, or 76.

10. The method of claim 8, wherein the modified oligonucleotide comprises at least one modified internucleoside linkage.

11. The method of claim 10, wherein the modified internucleoside linkage is a phosphorothioate internucleoside linkage.

12. The method of claim 10, wherein each internucleoside linkage of the modified oligonucleotide is a modified internucleoside linkage.

13. The method of claim 12, wherein the modified internucleoside linkage is a phosphorothioate internucleoside linkage.

14. The method of claim 1, wherein the SMN is SMN2 mRNA.

15. The method of claim 1, wherein the SMN is SMN2 pre-mRNA.

16. The method of claim 1, wherein the SMN is SMN2 protein.

17. The method of claim 1, wherein the cell is in a subject having one or more symptoms of SMA.

18. The method of claim 8, wherein the modified oligonucleotide comprises at least one nucleoside comprising a modified sugar.

19. The method of claim 18, wherein the modified sugar is a bicyclic sugar or 2'-O-methoxyethyl sugar.

20. The method of claim 8, wherein the modified oligonucleotide comprises:
a gap segment consisting of linked deoxynucleosides;
a 5' wing segment consisting of linked nucleosides; and
a 3' wing segment consisting of linked nucleosides;
wherein the gap segment is positioned between the 5' wing segment and the 3' wing segment and wherein each nucleoside of each wing segment comprises a modified sugar.

21. The method of claim 10, wherein each internucleoside linkage of the modified oligonucleotide is either a phosphodiester internucleoside linkage or a phosphorothioate internucleoside linkage.

* * * * *

UNITED STATES PATENT AND TRADEMARK OFFICE
CERTIFICATE OF CORRECTION

PATENT NO. : 10,851,371 B2
APPLICATION NO. : 15/565488
DATED : December 1, 2020
INVENTOR(S) : Rigo et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 279 days.

Signed and Sealed this
Tenth Day of January, 2023

Katherine Kelly Vidal
*Director of the United States Patent and Trademark Office*